(12) United States Patent
Allen et al.

(10) Patent No.: US 6,268,094 B1
(45) Date of Patent: Jul. 31, 2001

(54) PHOTOSENSITIVE MEDIA CARTRIDGE HAVING AN AMBIENT CONDITION SENSOR

(75) Inventors: Loretta E. Allen, Hilton; Yongcai Wang, Webster; Stephen M. Reinke, Rochester; Yeh-Hung Lai, Webster, all of NY (US)

(73) Assignee: Eastman Kodak Company, Rochester, NY (US)

( * ) Notice: Subject to any disclaimer, the term of this patent is extended or adjusted under 35 U.S.C. 154(b) by 0 days.

(21) Appl. No.: 09/597,999

(22) Filed: Jun. 19, 2000

(51) Int. Cl.[7] .................................................. G03C 1/00
(52) U.S. Cl. ............................................. 430/30; 430/496
(58) Field of Search ........................................ 430/30, 496

(56) References Cited

U.S. PATENT DOCUMENTS

| | | | |
|---|---|---|---|
| Re. 34,503 | 1/1994 | Sakakibara et al. | 355/27 |
| 4,044,366 | 8/1977 | Goto | 354/86 |
| 4,345,150 | 8/1982 | Tamura et al. | 250/339 |
| 4,399,209 | 8/1983 | Sanders et al. | 430/138 |
| 4,416,966 | 11/1983 | Sanders et al. | 430/138 |
| 4,440,846 | 4/1984 | Sanders et al. | 430/138 |
| 4,624,560 | 11/1986 | Beery | 355/27 |
| 4,648,699 | 3/1987 | Holycross et al. | 354/297 |
| 4,714,943 | 12/1987 | Sakakibara et al. | 355/27 |
| 4,727,385 | 2/1988 | Nishikawa et al. | 346/153.1 |
| 4,727,392 | 2/1988 | Stone et al. | 355/27 |
| 4,766,050 | 8/1988 | Jerry | 430/138 |
| 4,853,743 | 8/1989 | Nagumo et al. | 355/27 |
| 4,894,680 | 1/1990 | Hayakawa et al. | 355/27 |
| 4,943,827 | 7/1990 | Good et al. | 355/30 |
| 4,962,402 | 10/1990 | Ibuchi | 355/27 |
| 4,982,225 | 1/1991 | Sakakibara et al. | 355/30 |
| 5,028,954 | 7/1991 | Yamamoto et al. | 355/30 |
| 5,041,865 | 8/1991 | Asano et al. | 355/30 |
| 5,070,359 | 12/1991 | Nagata et al. | 355/27 |
| 5,091,743 | 2/1992 | Nagata et al. | 355/30 |
| 5,140,378 | 8/1992 | Ibuchi et al. | 355/295 |
| 5,146,274 | 9/1992 | Hattori et al. | 355/208 |
| 5,546,154 | 8/1996 | Raney et al. | 354/304 |
| 5,550,627 | 8/1996 | Dowler et al. | 355/326 M |
| 5,783,353 | 7/1998 | Camillus et al. | 430/138 |
| 5,884,114 | 3/1999 | Iwasaki | 396/583 |
| 5,916,727 | 6/1999 | Camillus et al. | 430/138 |
| 6,018,355 | 1/2000 | Kuwabara | 347/188 |

FOREIGN PATENT DOCUMENTS 0 864 430 A1   9/1998  (EP) .
0 980 026 A1   2/2000  (EP) .

OTHER PUBLICATIONS

USSN 09/557 031 filed on Apr. 20, 2000 titled Self–Contained Imaging Media Comprising Microencapsulated Color Formers by Yongcai Wang, Charles C. Anderson, Terry A. Heath and Kristine B. Lawrence.

*Primary Examiner*—Hoa Van Le
(74) *Attorney, Agent, or Firm*—David A. Novais

(57) ABSTRACT

A photosensitive media cartridge includes an ambient condition sensor mounted in the cartridge for sensing ambient conditions in the cartridge. When the cartridge is positioned at a media transfer position on an image forming device that permits the conveyance of media from the cartridge to the image forming device, image development or printing on the media in the image forming device is controlled based on the sensed ambient conditions in the cartridge.

14 Claims, 22 Drawing Sheets

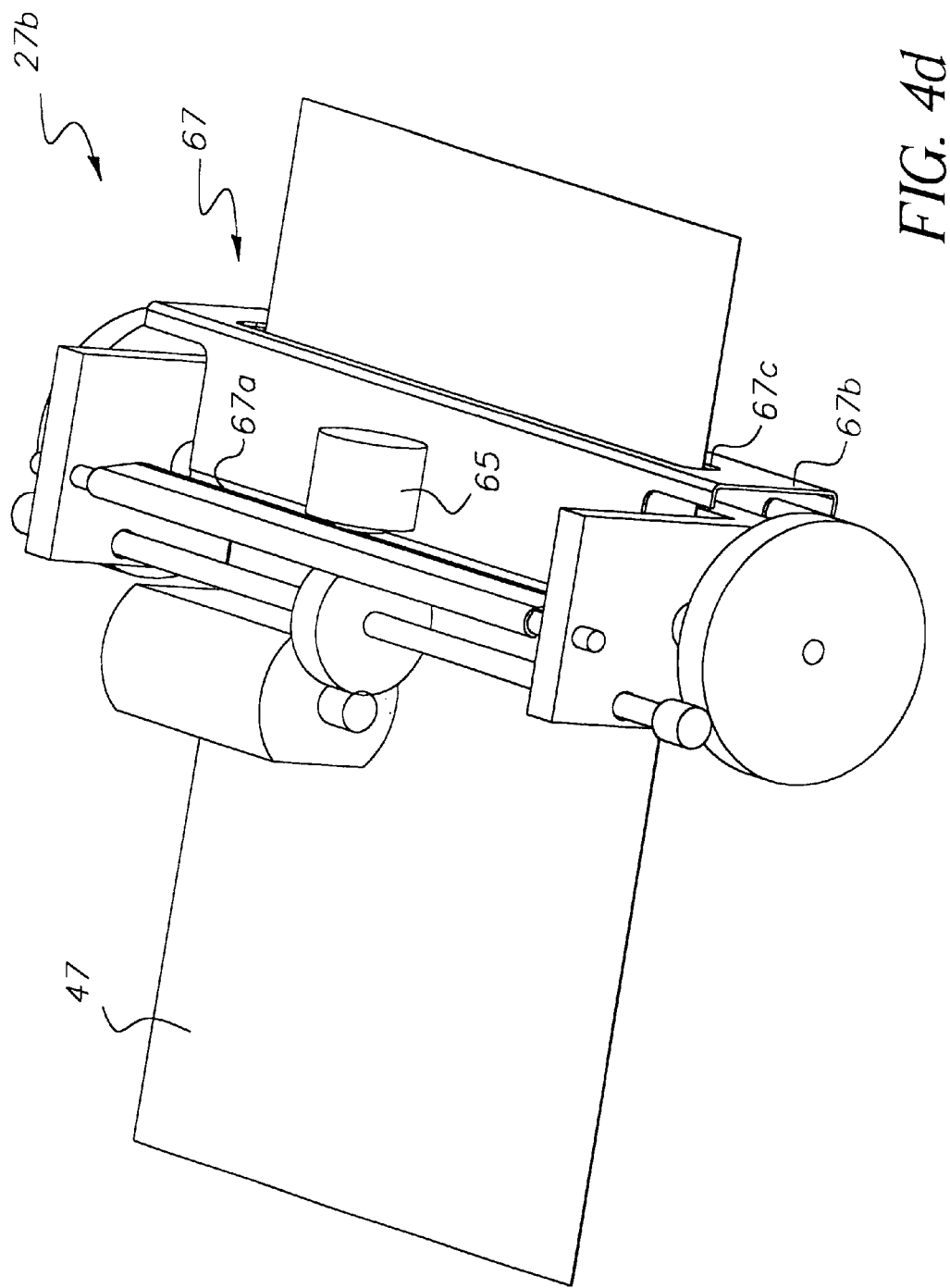

PHOTOSENSITIVE MEDIA CARTRIDGE HAVING AN AMBIENT CONDITION SENSOR

CROSS REFERENCE TO RELATED APPLICATIONS

Reference is made to commonly assigned copending applications Ser. No. 09/597,924 filed Jun. 19, 2000, entitled AN IMAGE FORMING DEVICE AND A METHOD OF PROCESSING PHOTOSENSITIVE MEDIA HAVING MICROENCAPSULATED IMAGING MATERIAL, filed concurrently herewith in the names of Loretta E. Allen, Yongcai Wang, Stephen M. Reinke and Yeh-Hung Lai; and Ser. No. 09/597,928 filed Jun. 19, 2000 entitled AN IMAGING ASSEMBLY AND MEDIA CARTRIDGE HAVING COOPERATING LINKAGE ARRANGEMENTS, filed concurrently herewith in the names of Loretta E. Allen, Yongcai Wang, Stephen M. Reinke and Yeh-Hung Lai.

FIELD OF THE INVENTION

The present invention relates to a photosensitive media cartridge having an ambient condition sensor for sensing ambient conditions within the cartridge. The present invention further relates to an imaging arrangement in which imaging of photosensitive material within an imaging device is controlled based on ambient conditions within the cartridge.

BACKGROUND OF THE INVENTION

Image forming devices which process a photosensitive media that includes microcapsules which encapsulate coloring material are known. In these imaging devices the microcapsules are exposed to a radiation based on image information. The microcapsules, whose mechanical strength can change when exposed to light, are ruptured by means of a crushing pressure, whereupon the coloring material and other substances encapsulated in the microcapsules flow out and development occurs. For example, some systems use a pair of upper and lower nip rollers to apply pressure. In these systems, the photosensitive media is passed between the pair of upper and lower nip rollers which apply pressure to the microcapsules to rupture the microcapsules and begin development. Imaging devices that employ microencapsulted photosensitive compositions are disclosed in U.S. Pat. Nos. 4,399,209, 4,416,966, 4,440,846, 4,766,050, 5,783,353, and 5,916,727.

A problem in processing photosensitive media having microencapsulated color forming material is that printing and/or imaging can be adversely affected by ambient conditions. That is, ambient conditions around a printer housing, around the photosensitive media, or in the cartridge which carries the photosensitive media can adversely affect subsequent printing or development of the image. More specifically, ambient conditions such as humidity around the printer housing, at the photosensitive media or in the cartridge which houses the photosensitive media can have adverse affects on the chemicals of the coloring material, the encapsulating material, and/or the photosensitive media. Further, the degree of hardening or curing of the microcapsules and the consequent increase in viscosity of the microcapsule varies with a change in humidity. As a result, photographic characteristics such as speed, minimum and maximum density, fogging density and full color imaging can be adversely affected.

SUMMARY OF THE INVENTION

The present invention provides for a media cartridge as well as an image forming device and method for processing photosensitive media that overcomes the above-mentioned drawbacks. More specifically, the present invention relates to an imaging device in which light sensitive media that contains light sensitive, rupturable microcapsules can be first exposed and then developed by applying pressure to the light sensitive media. In the image forming device of the present invention, print image quality can be improved by sensing ambient conditions such as humidity in the printer, directly from the media, or in the cartridge which carries the media, and adjusting at least one adjustable parameter based on the sensed ambient condition. As an example, in response to a sensed humidity condition, a controller or development member of the present invention can accordingly adjust the amount of pressure applied to the microcapsules.

As indicated above, in the imaging device of the present invention, the photosensitive medium contains light sensitive, rupturable microcapsules that are exposed and then developed by the application of pressure using a stylus or pinch rollers to rupture unexposed microcapsules. Thereafter, the developed print is fixed with heat supplied by a heater in the imaging device. In the present invention, the level of relative humidity can be sensed inside and/or outside of the printer, in the media cartridge or directly on the photosensitive media, and then at least one of the parameters of light exposure, developing pressure, printing speed or fixing temperature can be adjusted automatically on the basis of the relative humidity level to provide an improved image. As an example, by adjusting the printing speed for a printer, the so called "dark time" which is the time between exposure and development will be changed. The dark time affects the hardness of microcapsules and therefore their crushability. Also, within the context of the present invention, the concept of sensing the level of relative humidity on the photosensitive media refers to sensing the moisture content on the photosensitive media or material.

The imaging device of the present invention also includes an improved pressure assembly for applying a uniform pressure to the photosensitive media.

The present invention relates to a photosensitive media cartridge which comprises a housing for holding a stack of photosensitive media; and an ambient condition sensor mounted within the housing for sensing ambient conditions in the housing and providing an ambient condition signal indicative thereof, wherein a development of the photosensitive media is based on the sensed ambient condition. The ambient condition signal can also be indicative of rh storage levels of the photosensitive media.

The present invention further relates to an image forming arrangement which comprises an image forming device for forming a latent image on a photosensitive medium, with the photosensitive medium comprising a plurality of microcapsules which encapsulate imaging material. The image forming device comprises a pressure assembly for applying an initial pressure to the photosensitive medium to crush the microcapsules and develop a latent image on the photosensitive medium. The arrangement further includes a media cartridge for holding a stack of the photosensitive medium therein, with the media cartridge being adapted to be inserted into the image forming device to permit a conveyance of the photosensitive medium to the image forming device. The media cartridge comprises an ambient condition sensor mounted within the cartridge for sensing ambient conditions within the cartridge and providing an ambient condition signal indicative thereof to the pressure assembly, such that an amount of pressure applied by the pressure assembly is based on the ambient conditions sensed by the ambient condition sensor in the cartridge.

The present invention further relates to a method of controlling image development which comprises the steps of: providing an ambient condition sensor in a cartridge which holds photosensitive media therein, with the ambient condition sensor sensing ambient conditions within the cartridge and providing an ambient condition signal indicative thereof to a development member of a printer; inserting the cartridge to an insertion position in the printer which permits a passage of photosensitive media from the cartridge to the development member in the printer; and controlling a development of images on the photosensitive media based on the ambient condition signal received from the ambient condition sensor mounted in the cartridge.

BRIEF DESCRIPTION OF THE DRAWINGS

FIGS. 4(c)–4(d) are further views of the pressure applying assembly of FIG. 4(a);

DETAILED DESCRIPTION OF THE INVENTION

Figure 1:
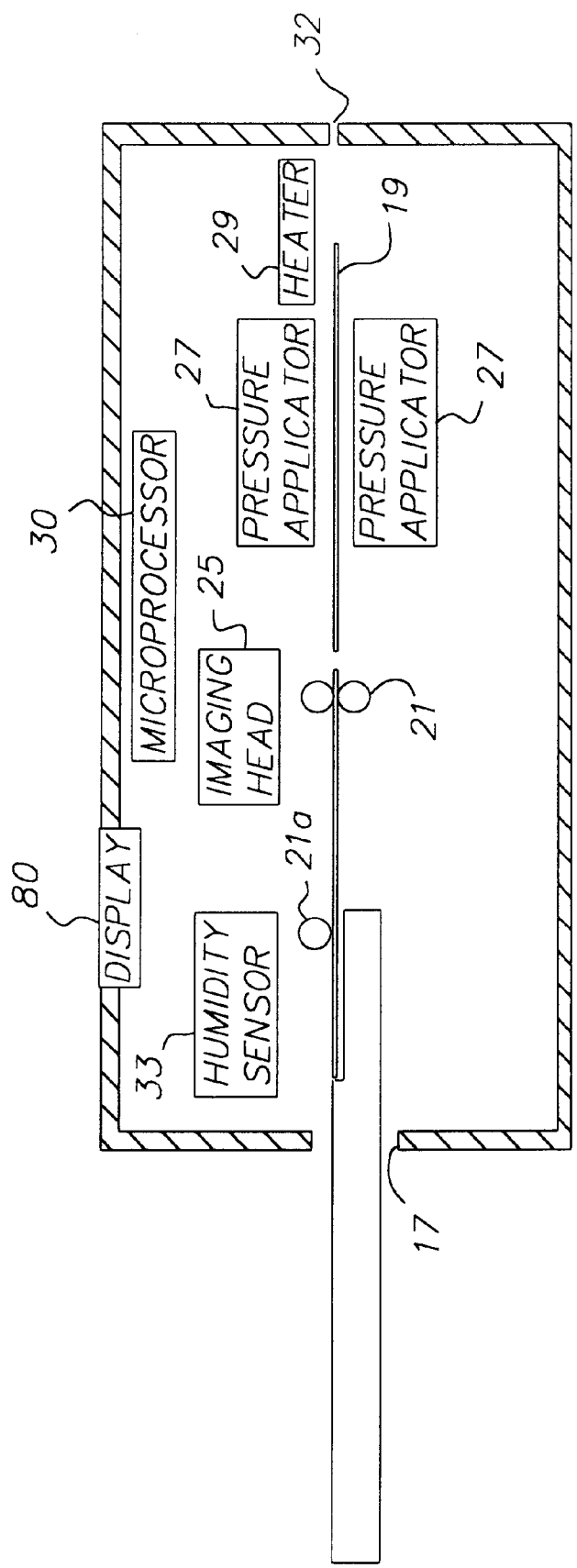
FIG. 1 schematically illustrates an image forming device in accordance with the present invention.

Referring now to the drawings, wherein like reference numerals represent identical or corresponding parts throughout the several views, FIG. 1 is a schematic view of an image forming device 15 of the present invention. Image forming device 15 could be, for example, a printer that includes an opening 17 which is adapted to receive a cartridge containing photosensitive media. As described in U.S. Pat. No. 5,884,114, the cartridge could be a light tight cartridge in which photosensitive sheets are piled one on top of each other. When inserted into image forming device 15, a feed mechanism which includes, for example, a feed roller 21a in image forming device 15, working in combination with a mechanism in the cartridge, cooperate with each other to pull one sheet at a time from the cartridge into image forming device 15 in a known manner. Once inside image forming device 15, photosensitive media travels along media path 19, and is transported by, for example, drive rollers 21 connected to, for example, a driving mechanism such as a motor. The photosensitive media will pass by an imaging head 25 which could include a plurality of light emitting elements that are effective to expose a latent image on the photosensitive media based on image information. After the latent image is formed, the photosensitive media is conveyed pass a development member such as a pressure applicator or pressure assembly 27, where an image such as a color image is formed based on the image information by applying pressure to microcapsules having imaging material encapsulated therein to crush the microcapsules. Within the context of the present invention, the imaging material comprises a coloring material (which is used to form images) or material for black and white media. After the formation of the image, the photosensitive media is conveyed pass a heater 29 for fixing the image on the media. In a through-feed unit, the photosensitive media could thereafter be withdrawn through an exit 32. As a further option, image forming device 15 can be a return unit in which the photosensitive media is conveyed or returned back to opening 17.

Figure 2:
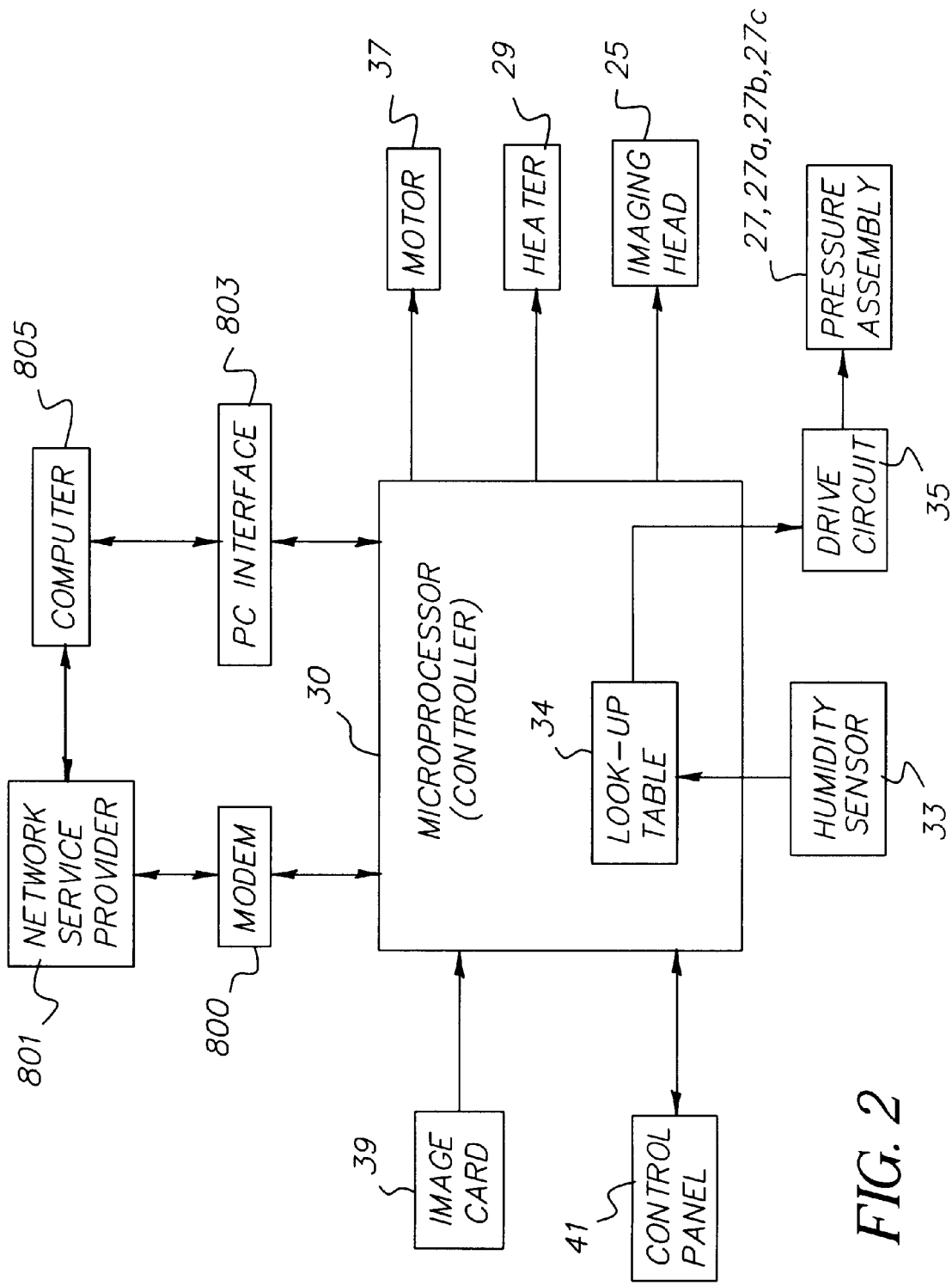
FIG. 2 schematically illustrates a microprocessor for controlling the operation of the image forming device of FIG. 1.

In a feature of the present invention, image forming device 15 includes a microprocessor or controller 30, illustrated in detail in FIG. 2. Controller 30 is effective to control several printing parameters with respect to the development of the image on the photosensitive media. For example, controller 30 can control parameters such as light exposure, pressure application, fixing temperature, printer motor speed, etc.

With reference to FIG. 2, a first feature of image forming device 15 and controller 30 of the present invention is the control of printing conditions based on sensed ambient conditions. More specifically, controller 30 is adapted to be responsive to ambient conditions to provide a pressure increasing or pressure decreasing signal to pressure assembly 27 to control the amount of pressure or crushing force applied by pressure assembly 27.

In one example of the invention as illustrated in FIG. 2, controller 30 is operationally associated with an ambient condition sensor which senses ambient conditions within image forming device 15. As shown in FIG. 2, the ambient condition sensor can be a humidity sensor 33 which senses humidity conditions within image forming device 15. As will be explained in detail later, the present invention is not limited to sensing the humidity within image forming device 15. It is noted that the humidity can be sensed outside of image forming device 15. It is further noted that the humidity can be sensed within a photosensitive media cartridge and/or directly from the photosensitive media itself For example, humidity or moisture content can be sensed directly from the media itself by measuring an IR absorption band of water within the media and comparing it to a reference value stored in controller 30. This is commonly called Near Infrared Spectroscopy, and can be done by sampling the media as it travels through the printer. As an example, U.S. Pat. No. 4,345,150 describes a method and apparatus for generating signals corresponding to the moisture content of paper by irradiating a sheet of paper with a near infrared ray, by detecting a beam having a coaction with the paper and accomplishing the desired arithmetic operations with the use of the detected signals.

Once the humidity is sensed by humidity sensor 33, a signal indicative thereof is sent to a look up table 34. Look up table 34 can include a plurality of reference humidity values which are compared to the sensed humidity value. Within the context of the present invention, the term reference humidity value refers to a humidity level or more preferably, a response curve (printing pressure vs. humidity). As a further option, rather than using a look-up table, an equation or a direct circuit can be utilized. Once this comparison is made, controller 30 can drive a drive circuit 35 for controlling the pressure application by pressure assembly 27. As an example, it is beneficial to apply a larger amount of pressure when a sensed humidity is high (for example, higher than a reference humidity value of 30%) and to reduce the pressure applied to the photosensitive material when the sensed humidity is low (for example, lower than a reference humidity value of 30%). Of course, it is noted that the present invention is not limited to the above-reference humidity value. It is noted that the reference humidity value can be any value which is set based on a desired result. As an example, a reference humidity value which provides consistent sensitometric properties can be used.

As a further example, it is beneficial to reduce the pressure applied to the photosensitive material, or increase the level of light exposure, or to reduce the printing speed when the sensed humidity is low. These changes can be done according to precalibrated information stored in the printer or stored on the cartridge through a barcode. Under certain conditions, it is desirable to change several parameters simultaneously according to the humidity information to optimize the printing conditions.

The precalibrated information for a given type of media can be obtained by testing the sensitometric characteristics of the media as a function of, for example, printing pressure or light exposure level. The details of response of printing pressure to humidity depend on the media. But it is in general theorized that the mechanical properties of a microcapsule containing layer changes with humidity which is turn changes the response of the microcapsule containing layer to printing pressure. For example, if the microcapsule containing layer is rigid at lower humidity (e.g. 30% RH) the microcapsules are more easily ruptured. If the microcapsule layer becomes more flexible at high humidity (e.g. 80%RH) the microcapsules are more difficult to rupture. This may change the amount of coloring materials released by the microcapsules during the printing process. Thus, the reference humidity depends on the type of media and level of light exposure.

Therefore, if the sensed humidity is higher than the reference humidity value, the drive circuit will provide a signal to pressure assembly 27 to increase the amount of pressure applied to the photosensitive medium, and if the humidity value is lower, the drive circuit will provide a signal to pressure assembly 27 to reduce the amount of pressure applied to the photosensitive medium.

As also indicated above, controller 30 is adapted to control features of imaging head 25, heater 29, as well as a motor 37 for driving rollers 21 and conveying media 47 through image forming device 15 to control printing speed. As a further option, these features could also be controlled based on the sensed humidity value. Further features of image forming device 15 and controller 30 include the provision of a control panel 41 to enable user control of image forming device 15, an image card 39 which can include image information with respect to the image which is to be developed and printed, and a display 80 for displaying information, such as image information or the sensed humidity value.

As a further option, images which are to be printed by image forming device 15 can be transferred or uploaded to image forming device 15 by way of the Internet or a computer. For example, as shown in FIG. 2, image forming device 15 or controller 30 can include a modem 800 for communication to a network service provider 801 such as the Internet. This permits a transfer of images to image forming device 15 from the Internet for subsequent printing. As a further example, image forming device 15 or controller 30 can include a PC interface 803 in communication with a computer 805 such as a personal computer. This permits the transfer of images stored in computer 805 to image forming device 15 for subsequent printing. As a further option, computer 805 can be communicated to Network service provider 801 to download images from the Internet to image forming device 15 via computer 805.

Figure 3A:
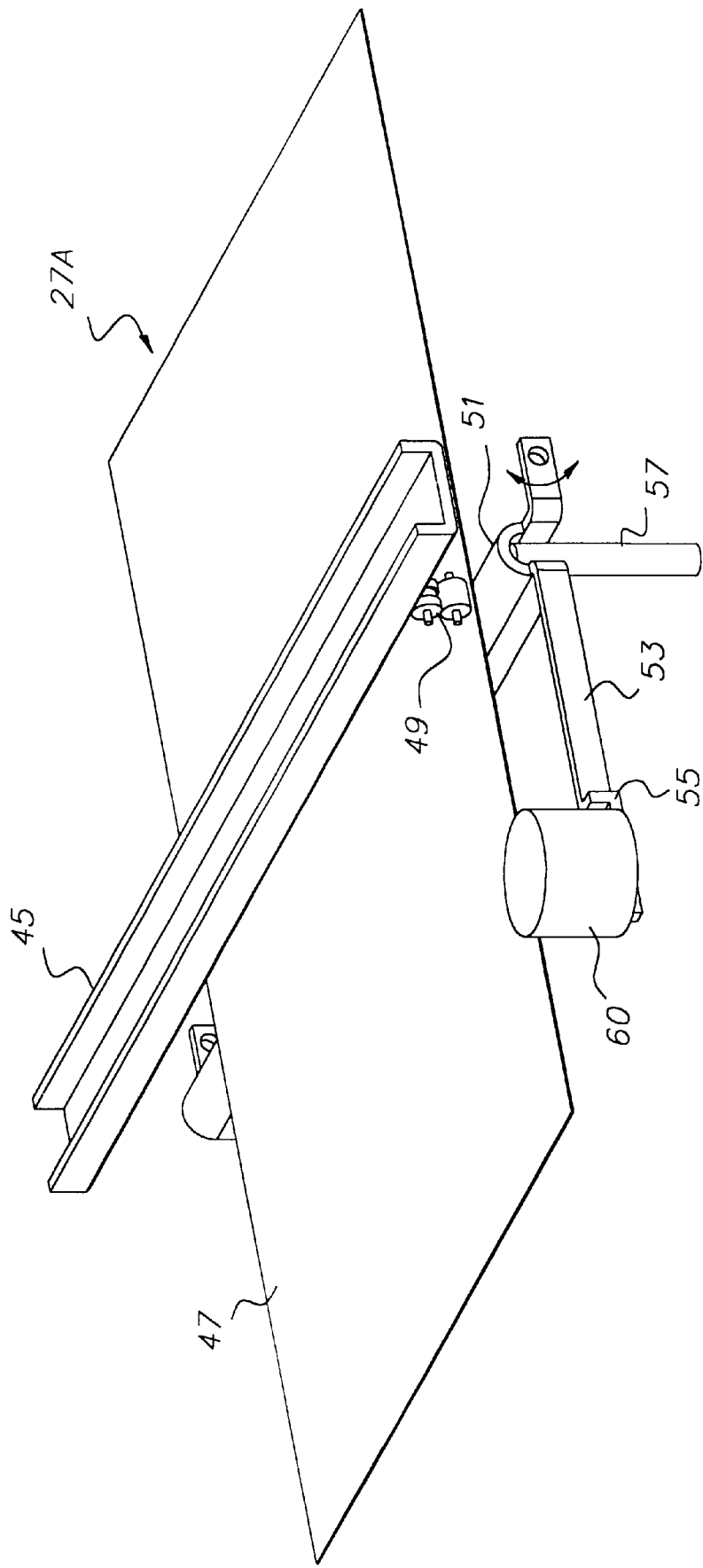
FIG. 3(a) illustrates a first embodiment of a pressure applying assembly of the image forming device of the present invention.
Figure 3B:
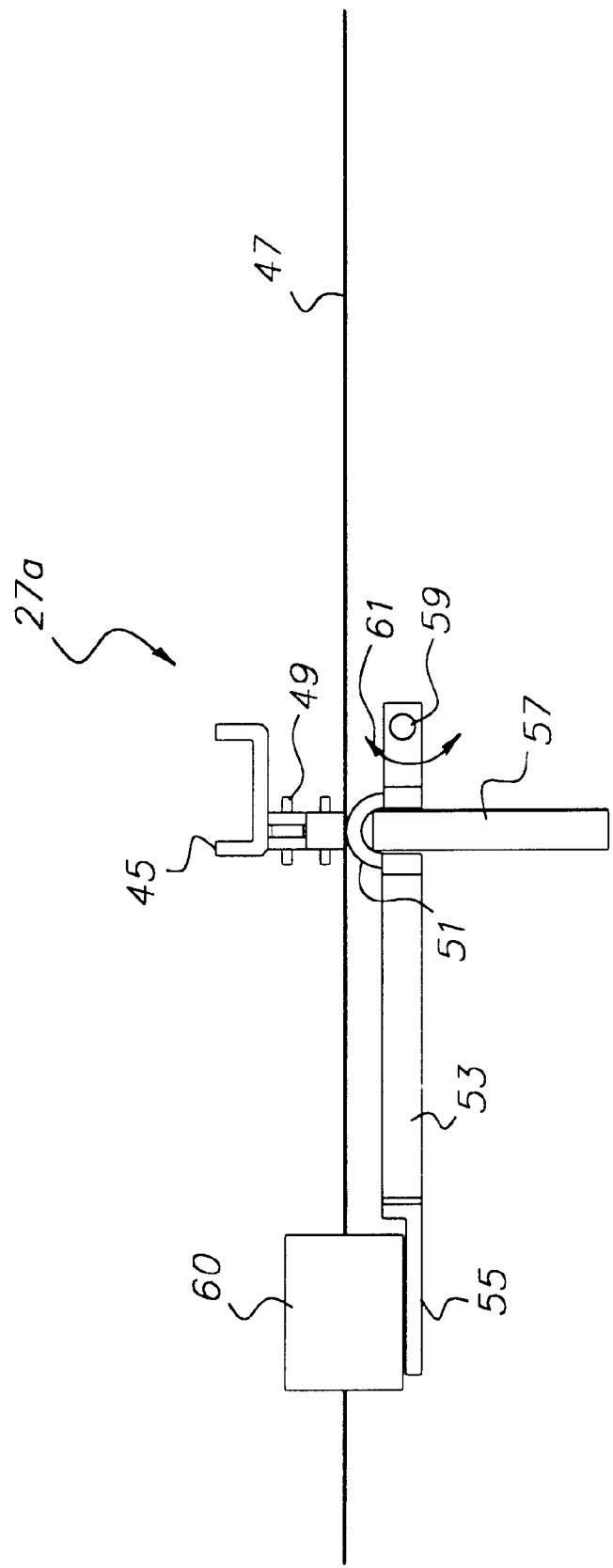
FIG. 3(b) is a side view of the pressure applying assembly of FIG. 3(a).
Figure 3C:
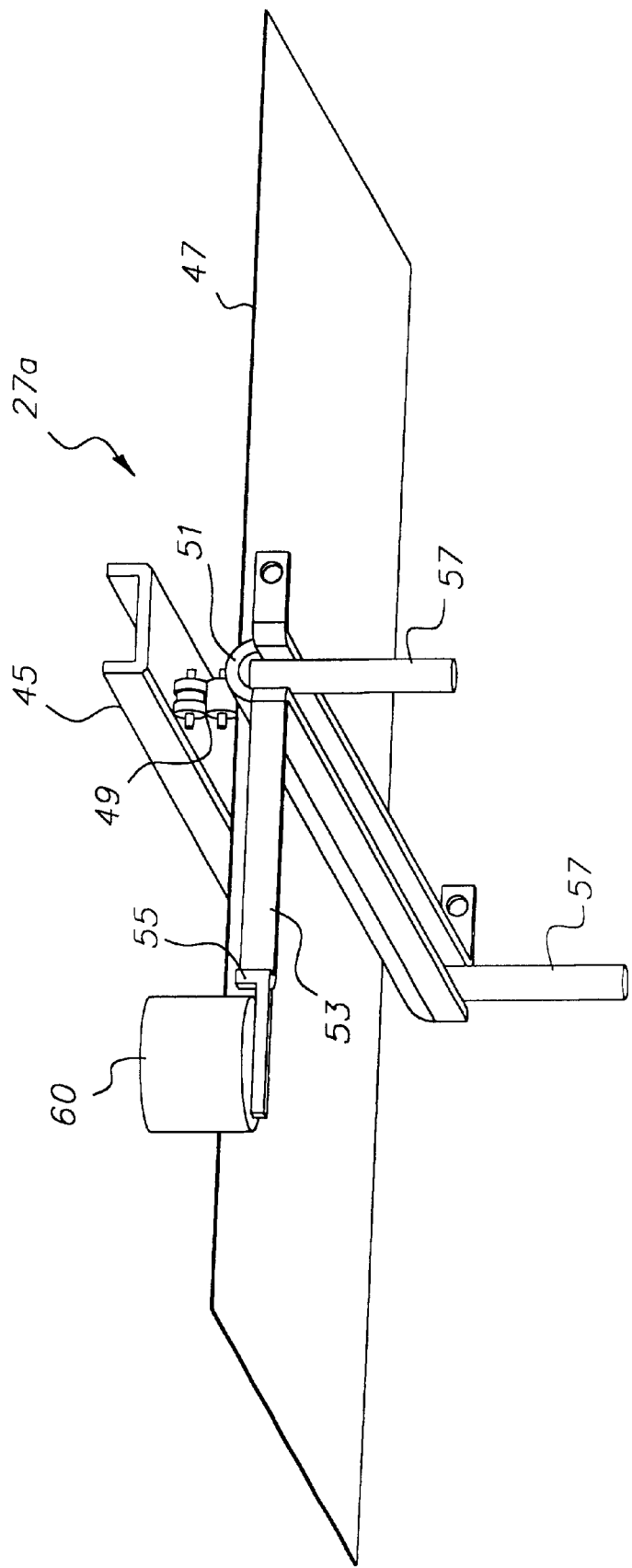
FIG. 3(c) is a further view of the pressure applying assembly of FIG. 3(a)

FIGS. 3(a), 3(b) and 3(c) illustrate different views of a first embodiment of pressure assembly 27 in accordance with the present invention. The pressure assembly is identified in FIGS. 3(a)–3(c) by reference numeral 27a. Pressure assembly 27a is a crushing roller and beam arrangement which provides a point contact on the photosensitive medium. More specifically, pressure assembly 27a includes a slide 45 which extends along a width-wise direction of a photosensitive medium 47. Moveably mounted on slide 45 is a crushing roller arrangement 49 which is adapted to move along the length of slide 45, i.e., across the width of photosensitive medium 47. Crushing roller arrangement 49 is adapted to contact one side of photosensitive medium 47. A beam 51 is positioned on an opposite side of photosensitive medium 47. Beam 51 is positioned so as to contact the opposite side of photosensitive medium 47 and is located opposite crushing roller 49. Beam 51 and crushing roller 49 when in contact with photosensitive medium 47 on opposite sides provide a point contact on photosensitive medium 47. Crushing roller 49 is adapted to move along a width-wise direction of photosensitive material 47 so as to crush microcapsules, release coloring material, and process image information such as image information provided by image card 39.

Extending from beam 51 is an arm 53 having an extension or seat portion 55. Also provided on beam 51 are compression springs 57 which urge beam 51 into contact with a lower side of photosensitive medium 47. It is further noted that beam 51 and arm 53 are pivotally mounted at a pivot point 59 so as to be movable or rotatable about pivot point 59 as illustrated by arrow 61. Thus, compression spring 57 urges beam 51 and arm 53 in a clockwise direction about pivot point 59, so as to urge beam 51 into contact with the lower surface of media 47. In a further feature of pressure assembly 27a as illustrated in FIGS. 3(a)–3(c), an electromagnet 60 is positioned adjacent to extension 55.

Thus, compression spring 57 urges beam 51 in a clockwise direction so as to place beam 51 in a pressure applying position. Electromagnet 60 mounted to a printer frame (not shown) applies an initial attraction force to extension 55 and arm 53 so as to help maintain beam 51 in the pressure applying position. As illustrated in FIG. 2, pressure assembly 27a receives a signal from controller 30. In the embodiment of FIGS. 3(a)–3(c), electromagnet 60 is operationally connected to controller 30 via drive circuit 35.

An operation of pressure assembly 27a will now be described. With reference to FIGS. 1 and 2, in one embodiment of the invention, a humidity within the housing of image forming device 15 is sensed by humidity sensor 33. This provides a signal to look up table 34 within controller 30. If the sensed humidity is above a humidity reference value or response curve, a pressure increasing signal will be applied to drive circuit 35 so as to increase the pressure applied by assembly 27a. More specifically, in response to a pressure increasing signal, controller 30 will interact with electromagnet 60 to increase the attraction force on extension 55 and in turn on arm 53, and therefore increase the initial attraction force to further pivot arm 53 and beam 51 in the clockwise direction towards photosensitive media 47. This increases the pressure applied by beam 51 on photosensitive media 47, and increases the crushing force applied to the microcapsules via beam 51 and crushing roller 49. If the humidity sensed by humidity sensor 33 is below a reference humidity value, controller 30 will provide a signal to drive circuit 35 to decrease the pressure applied by pressure assembly 27a. In this scenario, controller 30 will interact with electromagnet 60 to reduce the attraction force back to the initial attraction force. Thus, when electromagnet 60 receives a signal from controller 30 indicating that the sensed humidity is lower than a reference humidity, a pressure decreasing signal is provided by controller 30 to electromagnet 60. The signal causes electromagnet 60 to reduce the attraction force against arm 53 back to the initial attraction force, and thus return beam 51 and arm 53 to its initial pressure applying position.

Figure 4A:
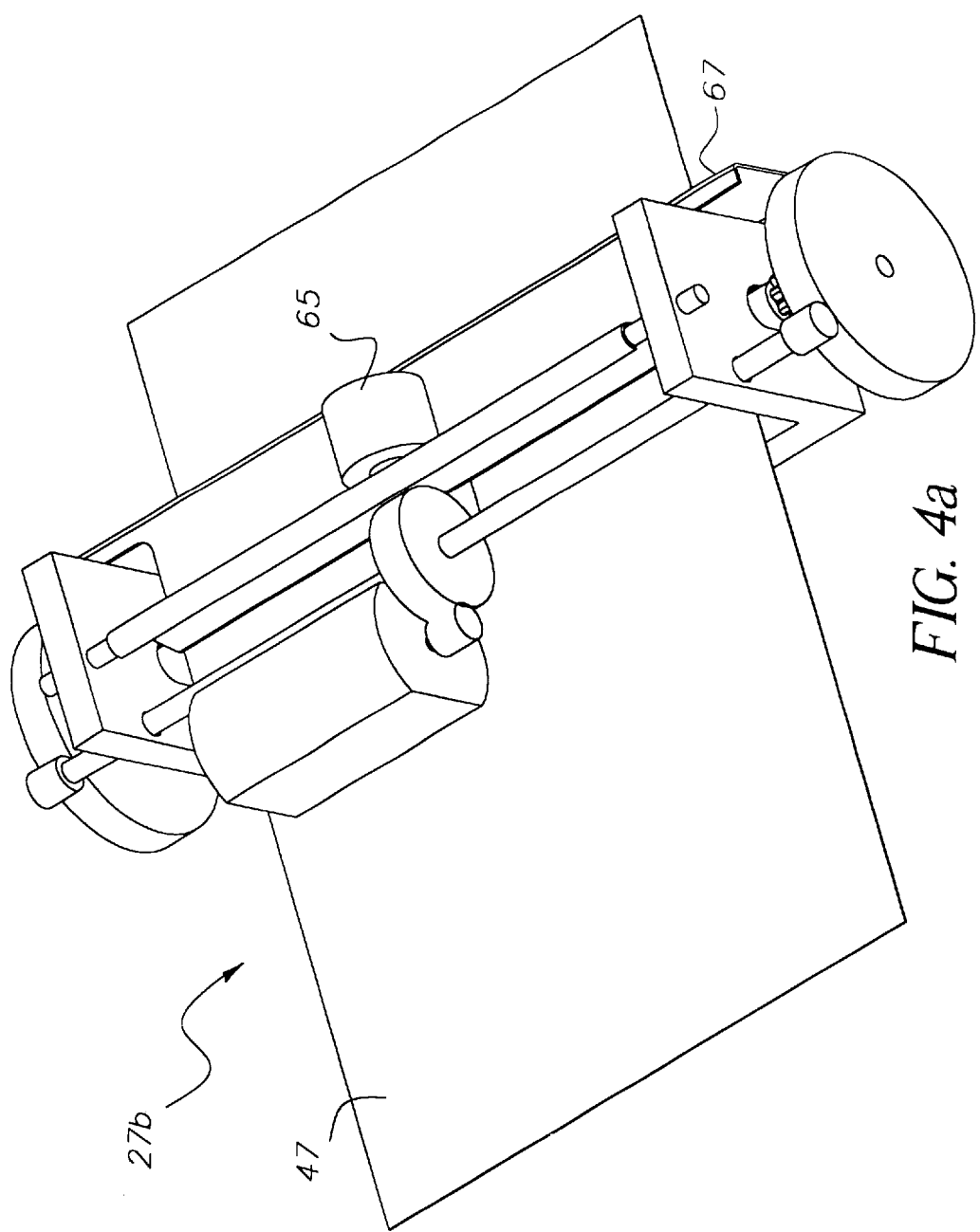
FIG. 4(a) is a view of a second embodiment of a pressure applying assembly of the image forming device of the present invention.
Figure 4B:
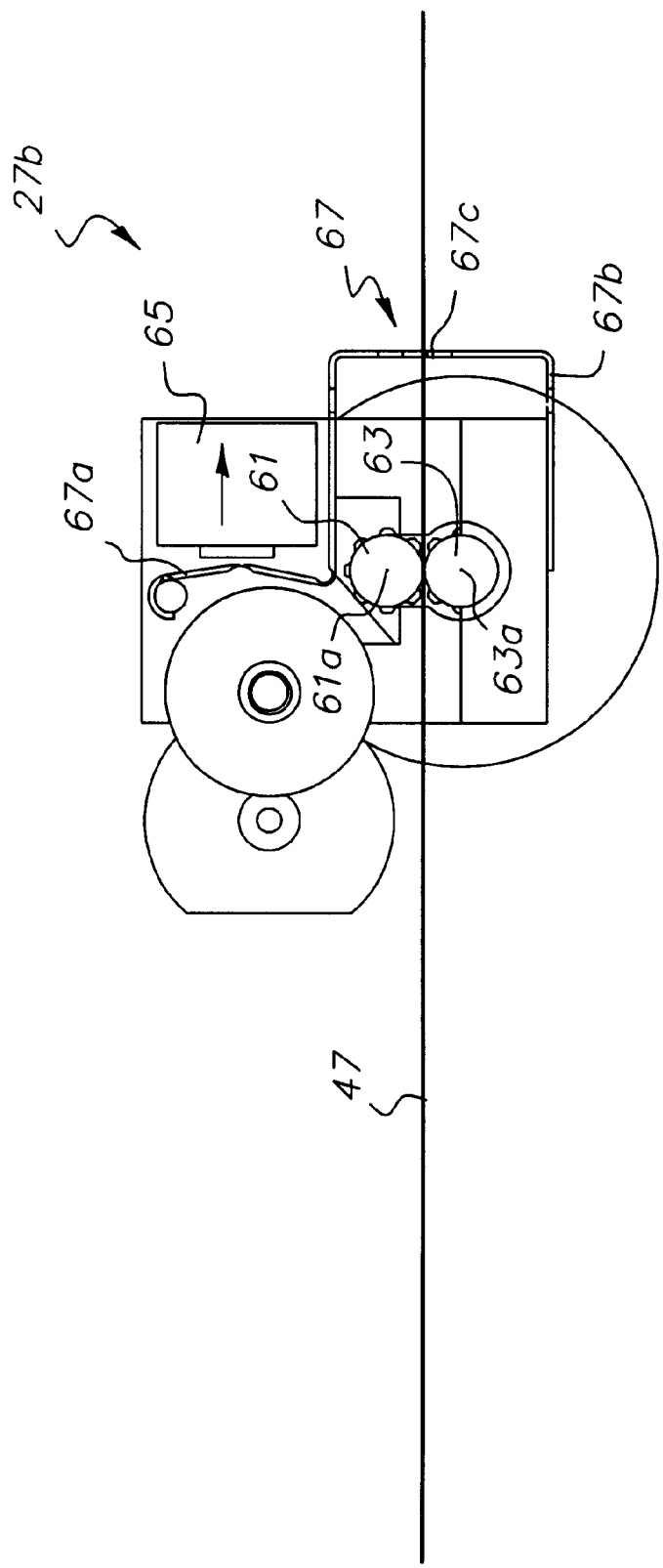
FIG. 4(b) is a side view of the pressure assembly of FIG. 4(a)
Figure 4C:
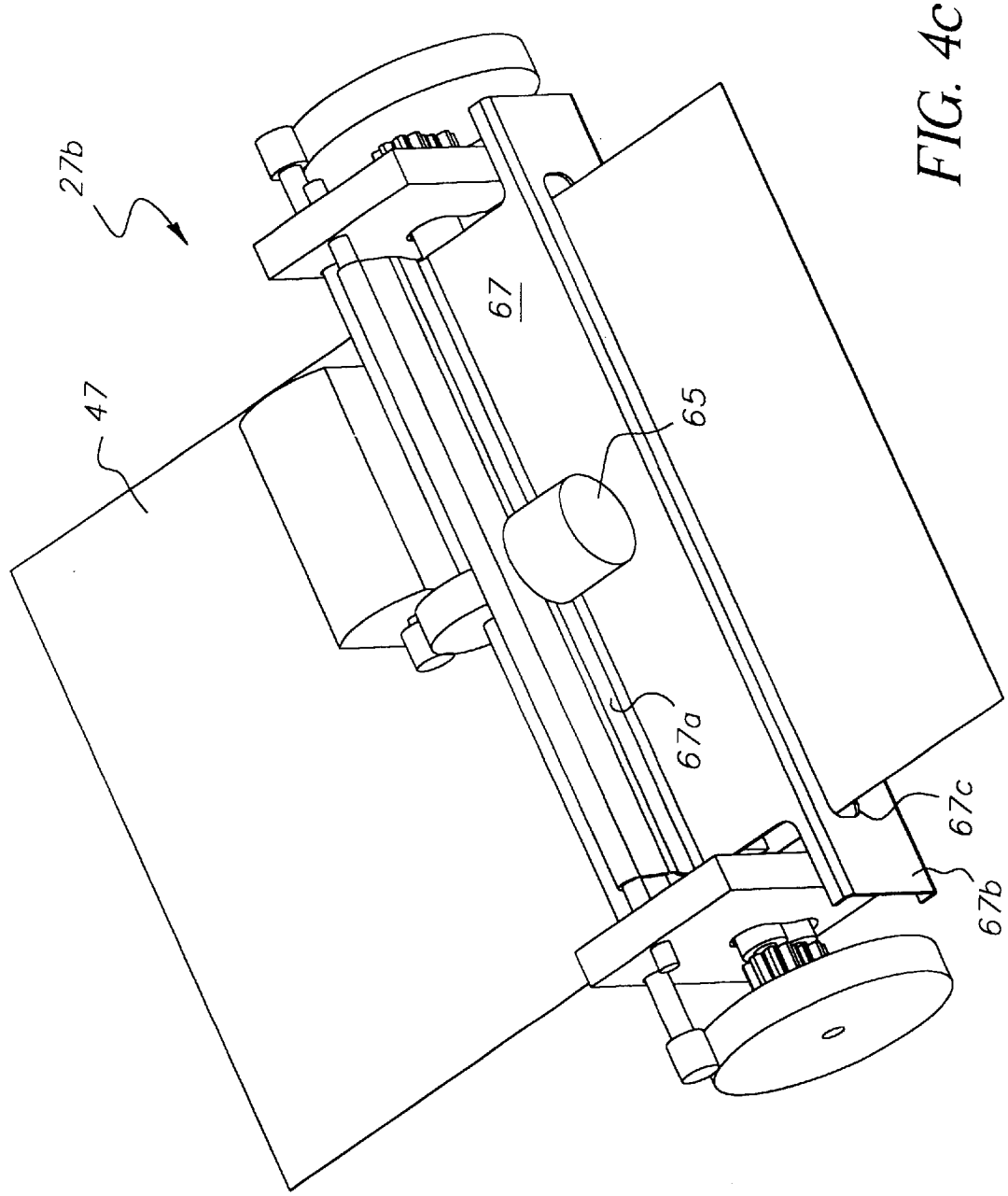

FIGS. 4(a)–4(d) illustrate different views of a second embodiment of pressure assembly 27 of the present invention. The pressure assembly in FIGS. 4(a)–4(d) is referenced by reference numeral 27b. In the embodiment of FIGS. 4(a)–4(d), photosensitive media 47 including rupturable microcapsules are first exposed as described with reference FIG. 1, and then developed by pressure pinch rollers 61, 63 which form a nip as illustrated in FIG. 4(b). The embodiment of FIGS. 4(a)–4(d) illustrates a roller contact on each side of photosensitive media 47. In the embodiment of FIGS. 4(a)–4(d) one of the rollers (roller 63) includes a fixed axis 63a, and the other roller (roller 61) includes a floating axis 61a. Rollers 61 and 63 are mounted on a full length clamping spring 67 which has a fixed part or section 67b onto which roller 63 is rotatably mounted, and an adjustable part or section 67a onto which roller 61 is rotatably mounted. Fixed section 67b includes a slot 67c to permit the passage of photosensitive material therethrough. In a feature of the invention as illustrated in FIGS. 4(a)–4(d), clamping spring 67 forms a toggle which permits an increase or decrease in the pressure applied to roller 61 having floating axis 61a. Clamping spring 67 further permits a uniform application of pressure at the nip of the first and second rollers 61 and 63 across an entire width of photosensitive medium 47, and maintains the first and second rollers 61 and 63 in a pressure applying position.

As described above, clamping spring 67 has a section 67b which rotatably holds roller 63 so that roller 63 has a fixed rotational axis 63a. The other section 67a of clamping spring 67 rotatably holds roller 61 so that roller 61 has an adjustable axis 61a that is movable toward and away from roller 63. In one feature of the present invention, in order to move section 67a of clamping spring 67, an electromagnet 65 is mounted or placed in the vicinity of section 67a of clamping spring 67. Magnet 65 is operationally associated with controller 30 for controlling the positioning of roller 61 with respect to roller 63.

Therefore, in the same manner as the embodiment of FIGS. 3(a)–3(c), if a humidity within the housing sensed by humidity sensor 33 is below a reference humidity as stored in look-up Table 34 (FIG. 2), a pressure decreasing signal is provided from controller 30 to drive circuit 35, so as to cause pressure assembly 27b to reduce the pressure applied to photosensitive media 47. That is, controller 30 will interact with magnet 65 to apply a magnetic force to section 67a of clamping spring 67 and reduce the force roller 61 applies to roller 63.

If the humidity sensed by humidity sensor 33 is greater than a reference humidity value or response curve as stored in look-up Table 34, controller 33 provides a signal to drive circuit 35 to increase the pressure applied by pressure assembly 27b. In this mode, controller 30 will provide a signal to magnet 65 to reduce the attractive force acting on clamping spring 67a and urge roller 61 further into contact with roller 63. This increases the pressure applied on photosensitive medium 47.

Figure 5A:
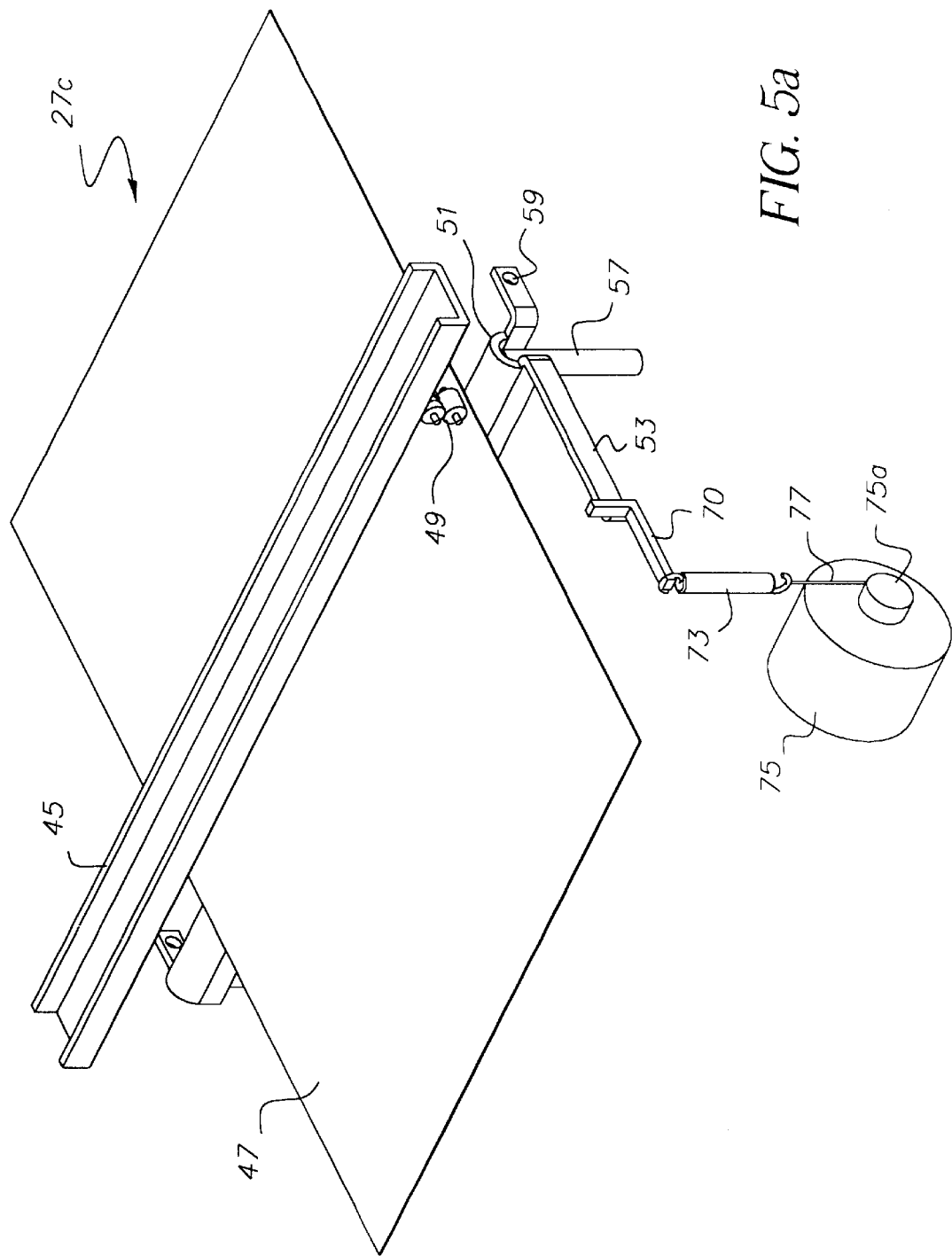
FIGS. 5(a)–5(b) are views of a further embodiment of a pressure applying assembly of the image forming device of the present invention.
Figure 5B:
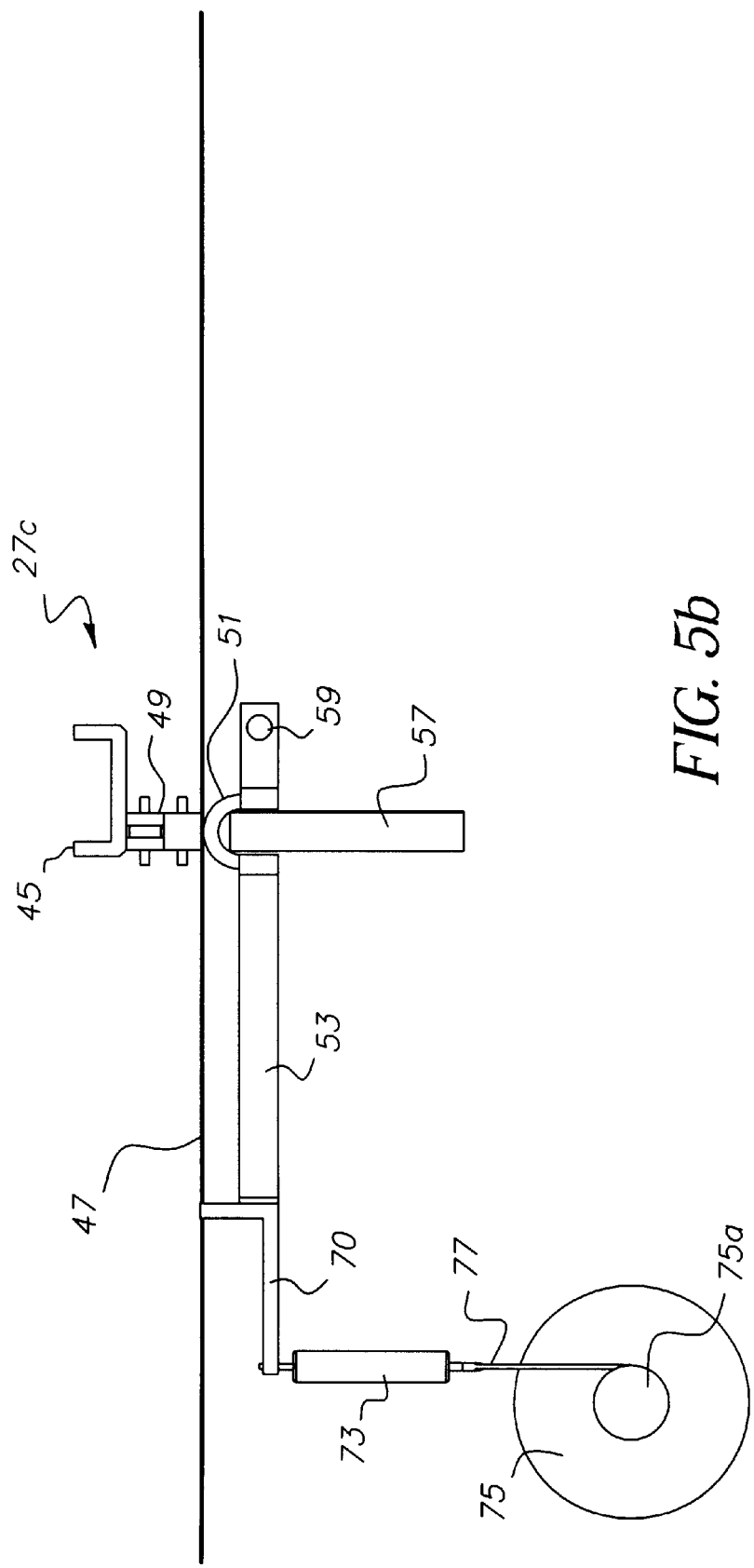

FIGS. 5(a)–5(b) illustrate different views of a further embodiment of pressure assembly 27. In FIGS. 5(a)–5(b), the pressure assembly is identified by reference numeral 27c. As illustrated in FIGS. 5(a)–5(b), pressure assembly 27c includes beam 51 and arm 53 which are movable about pivot point 59 as in the embodiment of FIGS. 3(a)–3(c). Beam 51 contacts one side of photosensitive material 47. On the opposite side of photosensitive material 47 slide 45 provides a guide for crushing roller 49 so as to guide crushing roller 49 across the width of photosensitive material 47, as also described with reference to FIGS. 3(a)–3(c). Pressure assembly 27c in FIGS. 5(a)–5(b) differs from pressure assembly 27a illustrated in FIGS. 3(a)–3(c) with respect to using the combination of a stepper motor 75 and a spring 73 as opposed to an electromagnet. More specifically, as shown in FIGS. 5(a)–5(b), pressure assembly 27c includes an extension portion 70 which extends from arm 53, onto which is mounted extension spring 73. A cable 77 leads from extension spring 73 and is wrapped around a pulley 75a of stepper motor 75. Therefore, in the embodiment of FIGS. 5(a)–5(b), stepper motor 75 can vary the pulley rotational position and the attached cable 77 to result in a varying length of extension spring 73. By pulling down on extension spring 73, the crushing roller force on the media by beam 51 is reduced.

More specifically, in response to a high humidity signal from controller 30 in which the measured humidity is higher than a reference humidity as described with respect to FIGS. 3(a)–3(c), controller 30 provides a pressure increasing signal to stepper motor 75. This causes stepper motor 75 to rotate in a counter clockwise direction so as to urge beam 51 and arm 53 in a clockwise rotation about pivot 59. This causes an increase in the force applied by beam 51 onto photosensitive media 47. In the event that the humidity sensed is lower than a reference humidity, a pressure decreasing signal is provided by controller 30. Therefore, controller 30 will interact with stepper motor 75 to rotate stepper motor 75 in a clockwise direction so as to pull down arm 53 and beam 51 and rotate beam 51 and arm 53 in a counter clockwise direction about pivot 59. This serves to reduce the amount of crushing force applied by beam 51 onto photosensitive media 47. Further, as in the embodiment of FIGS. 3(a)–3(c), a compression spring 57 is provided on beam 51, so as to maintain an initial pressure of beam 51 onto photosensitive media 47.

Figure 6A:
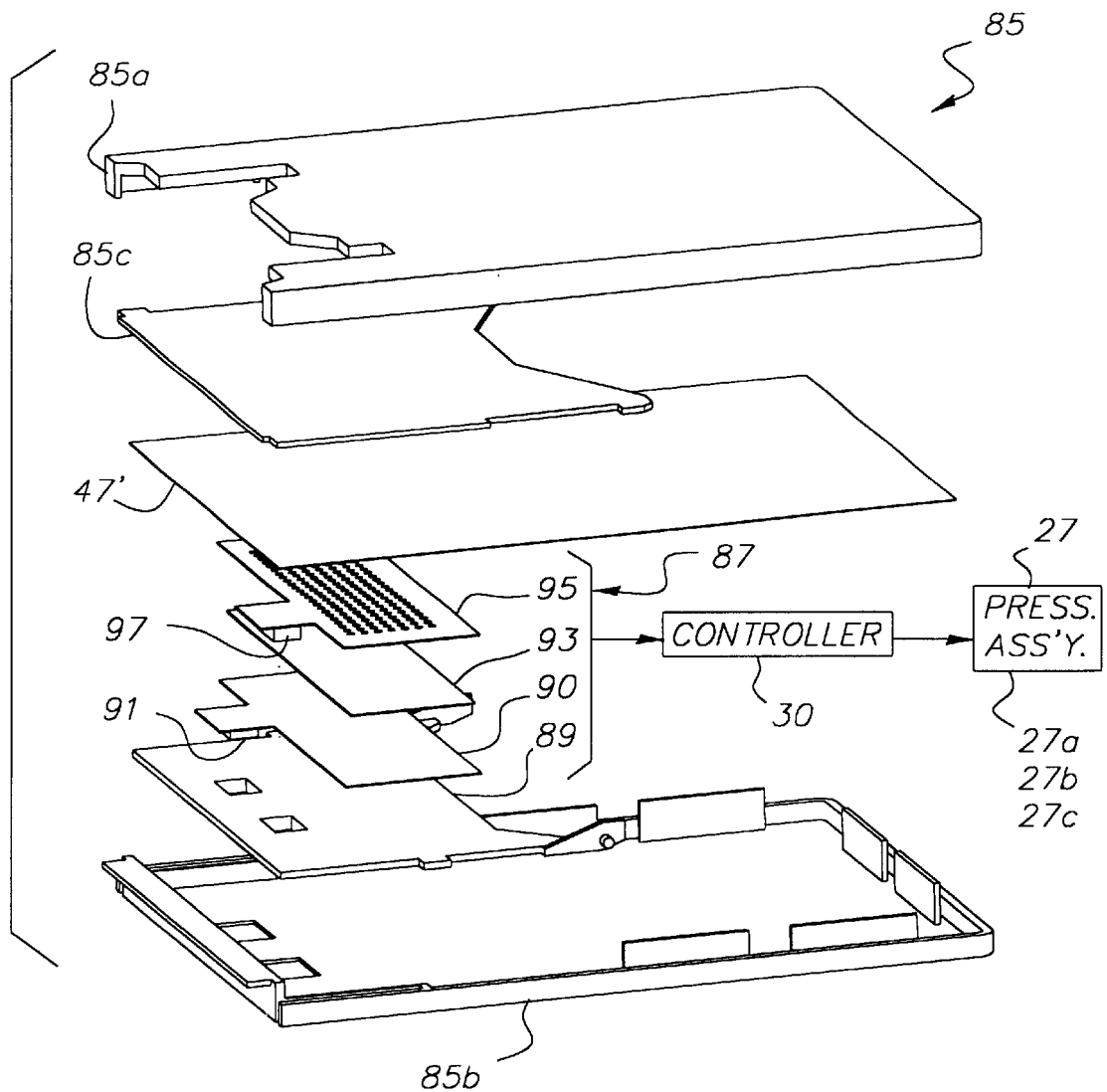
FIG. 6(a) shows a device for sensing ambient conditions in a photosensitive media cartridge in accordance with a feature of the present invention.

The present invention has thus for been described with respect to measuring ambient conditions such as humidity within the housing of image forming device 15. As previously indicated, the present invention is not limited to such an arrangement. For example, as a further option, the humidity within a cartridge which holds photosensitive media that is to be fed into image forming device 15 can be sensed. FIG. 6(a) illustrates one embodiment for sensing humidity within a cartridge.

More specifically, FIG. 6(a) is an exploded view of a cartridge 85 that holds photosensitive media 47'. Media 47' could be of the type having microcapsules with coloring material. As shown in FIG. 6(a), media cartridge 85 defines a housing having top and bottom sections 85a, 85b which can snap together to house media 47' therein, one on top of the other. Cartridge 85 further includes a light-lock door 85c. Cartridge 85 and more specifically, one of the sections 85a, 85b of cartridge 85 includes a humidity sensor 87 which comprises a first spring plate 89 that is adapted to be mounted on, for example, section 85b. Mounted on spring plate 89 is a first contact plate 90 having a first electrode 91 and a second contact plate 95 having a second electrode 97. Sandwiched between first and second contact plates 90 and 95 is a sampling member or dielectric layer 93. Sampling member 93 could be a material which is successible or responsive to humidity conditions within cartridge 85. An example of this could be a salt solution impregnated fabric or various hydrophilic polymers.

Therefore, in the arrangement of FIG. 6(a), electrodes 97 and 91 provide for a capacitor and the measured humidity is a function of capacitance. Electrodes 97 and 91 protrude through cut-outs in spring plate 89 to make physical contact between sensor 87 located within cartridge 85 and controller 30 located within image forming device 15. Based on the signal from humidity sensor 87, controller 30 controls the application of pressure by way of pressure assembly (27a, 27b, 27c) in the manner described with respect to FIGS. 3(a)–3(c); 4(a)–4(d); and 5(a)–5(b). Humidity sensor 87 as illustrated in FIG. 6(a) can replace humidity sensor 33 in the housing of image forming device 15 or be used in addition to sensor 33. As previously described, a higher humidity would provide a signal to increase the pressure applied by either one of pressure assemblies 27a, 27b or 27c, while a lower humidity would provide a signal to controller 30 to control the pressure assemblies to lower the crushing pressure. Thus, the combination of the cartridge and the image forming device would provide for an image forming assembly or arrangement.

Figure 6B:
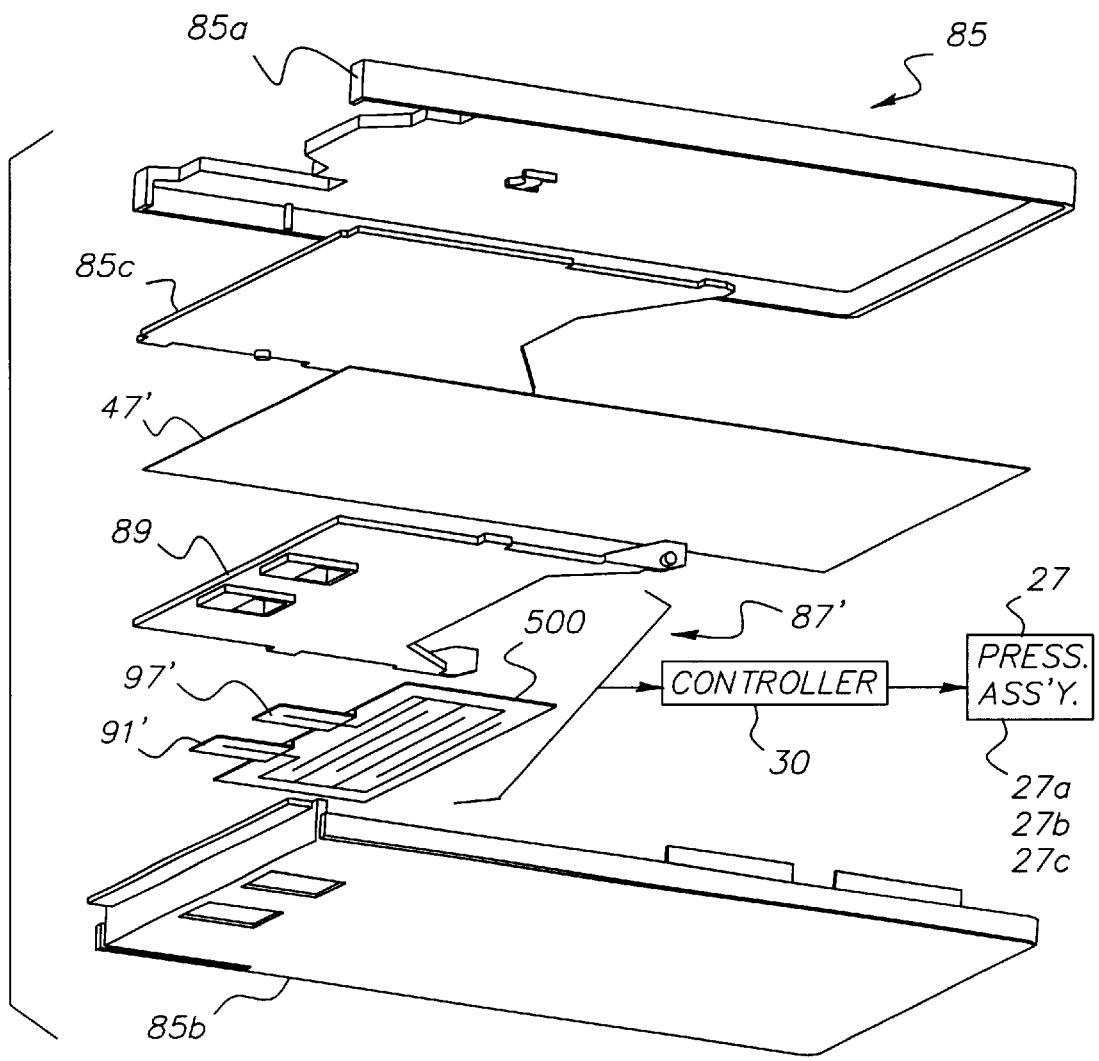
FIG. 6(b) shows another device for sensing ambient conditions in a photosensitive media cartridge in accordance with a feature of the present invention.

FIG. 6(b) illustrates another embodiment for sensing humidity within a cartridge. More specifically, FIG. 6(b) is an exploded view of a cartridge 85 that holds photosensitive media 47'. Media 47' could be of the type having microcapsules with coloring material. As shown in FIG. 6(b), media cartridge 85 defines a housing having top and bottom sections 85a, 85b which can snap together to house media 47' therein, one on top of the other. Cartridge 85 and more specifically, one of the sections 85a, 85b of cartridge 85 includes a humidity sensor 87' which comprises a substrate 500 with interdigitated conductive terminals on the substrate overcoated with a humidity sensitive material such as a hydrophilic polymer. Humidity effects the electrical properties of the polymer and the relative humidity can be obtained directly from the equivalent resistance or conductance of the sensor. Electrodes 91' and 97' protrude through cut-outs in spring plate 89' to make physical contact between sensor 87' located within cartridge 85 and controller 30 located within image forming device 15.

Figure 6C:
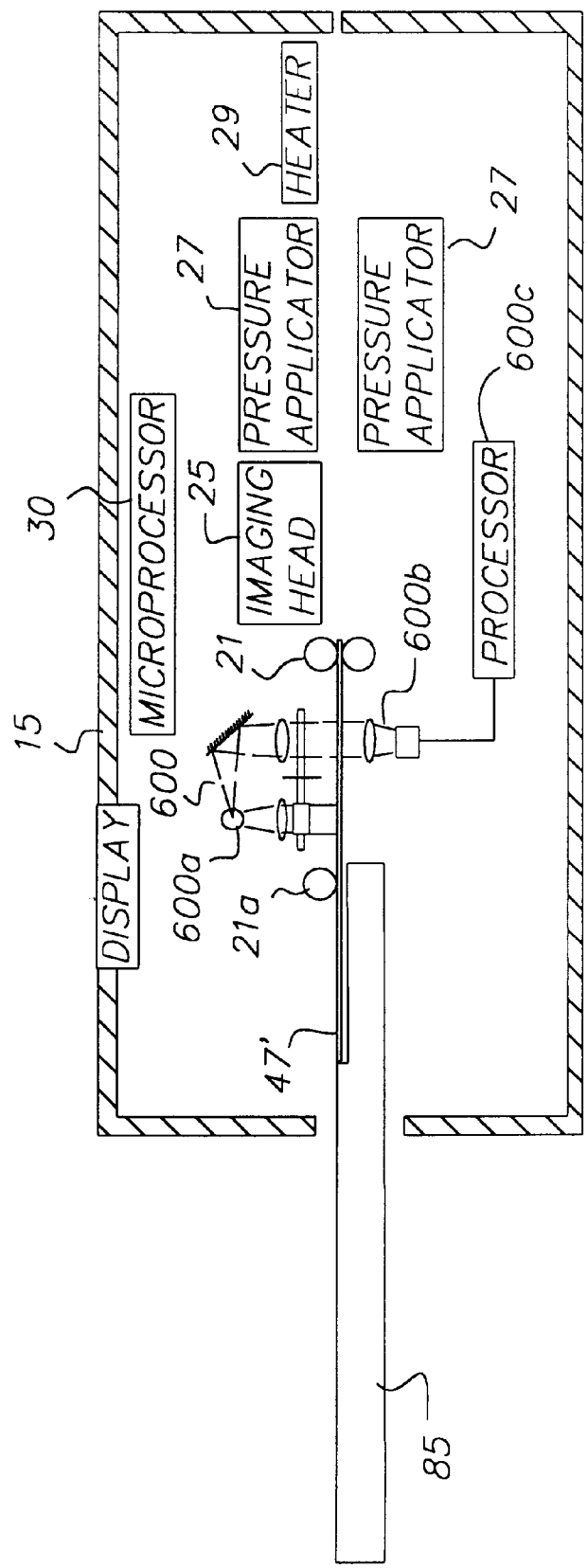
FIG. 6(c) shows another device for sensing moisture content in a photosensitive media in accordance with feature of the present invention.

FIG. 6(c) illustrates an embodiment for sensing moisture content of photosensitive media 47'. Media 47' could be of the type having microcapsules with coloring material. As shown in FIG. 6(c), photosensitive media 47' is drawn out of cartridge 85 into image forming device 15. A device 600 to measure the moisture content of photosensitive media 47' is positioned within image forming device 15, and in the media path between the exit of cartridge 85 and imaging head 25 (see, for example, U.S. Pat. No. 4,345,150). Device 600 to measure the moisture content of media 47' comprises a near infrared light source 600a to irradiate media 47' having a first wavelength which is more absorbed by the moisture and a reference wavelength which is less absorbed by the moisture, a detecting arrangement 600b and a processor 600c. Based on the signal from processor 600c, controller 30 controls the application of pressure by way of pressure assembly (27a, 27b, 27c).

Figure 7:
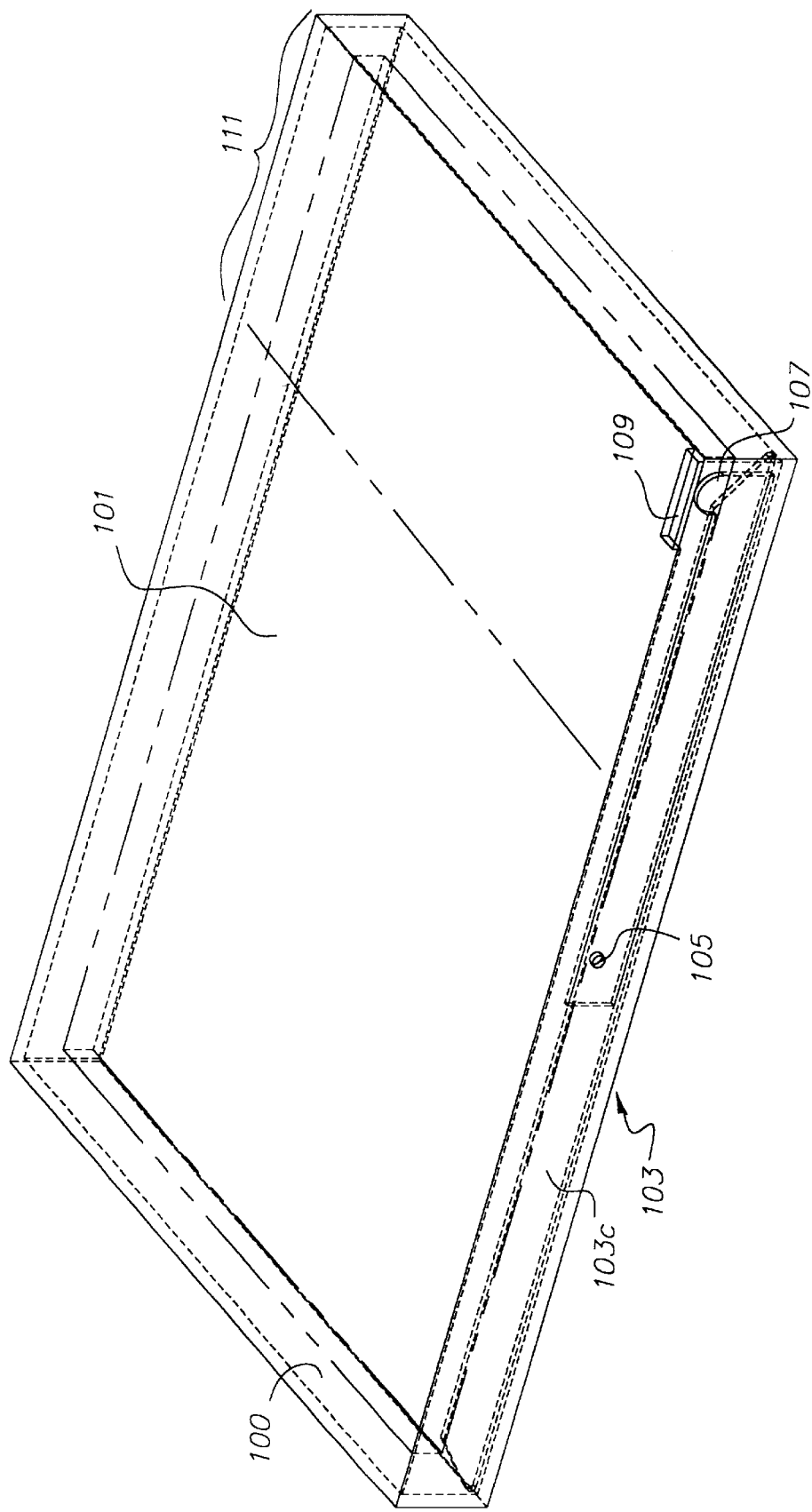
FIG. 7 is a further embodiment of the present invention including a linkage assembly within a photosensitive media cartridge for adjusting a pressure applied to the photosensitive media during development.
Figure 8A:
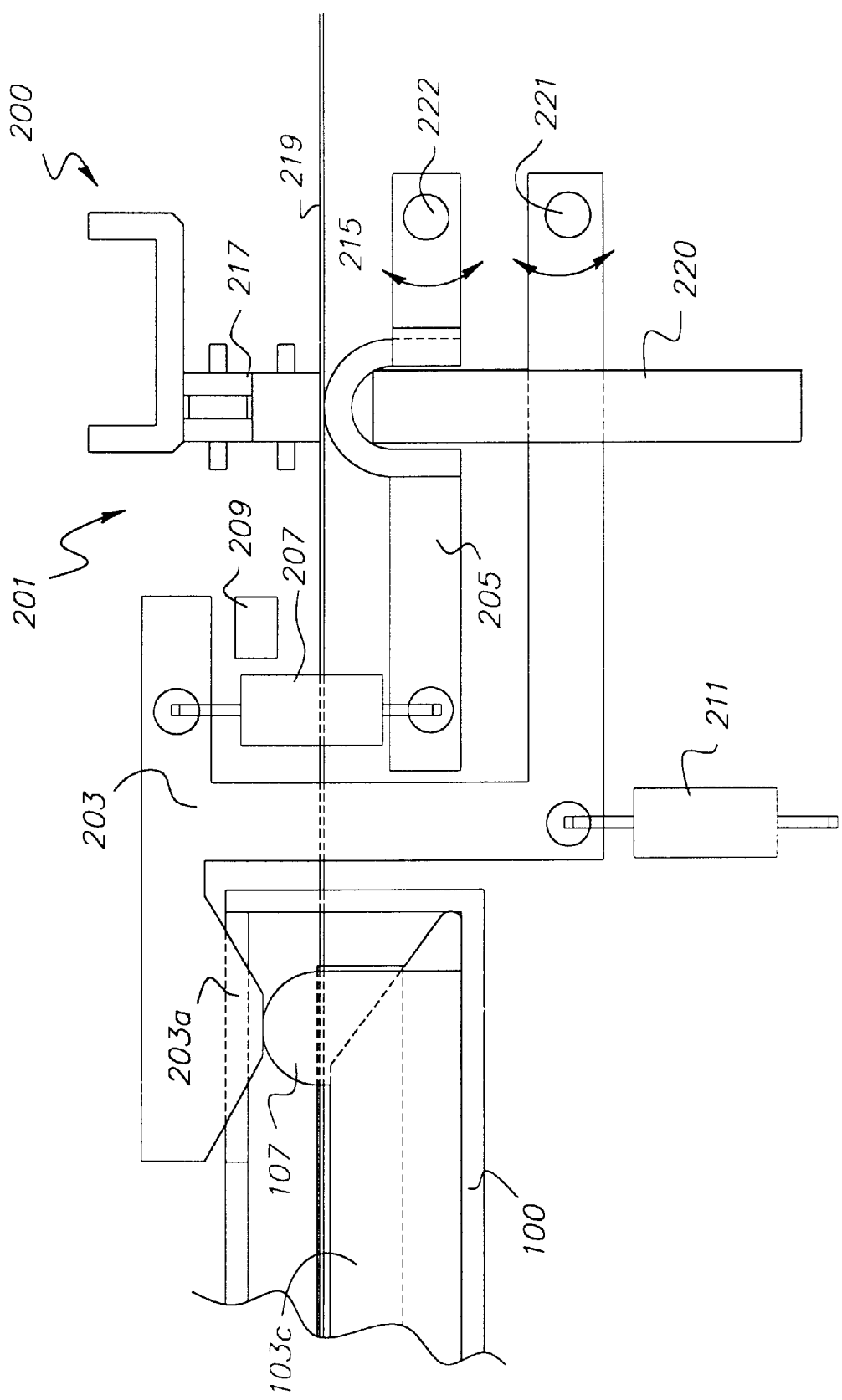
FIGS. 8(a)–8(b) are detailed views of the linkage assembly and its cooperation with a pressure applying assembly of an image forming device.
Figure 8B:
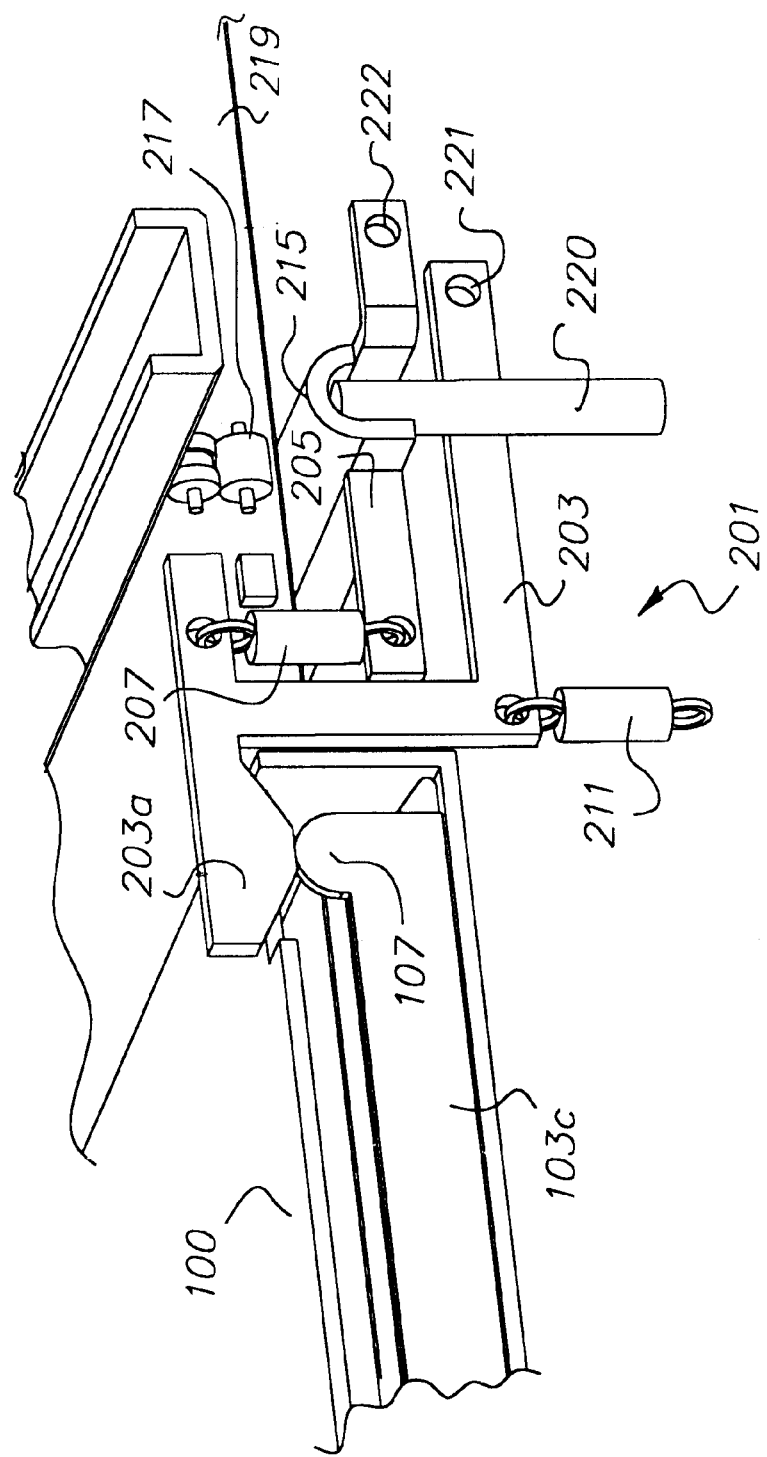
Figure 9:
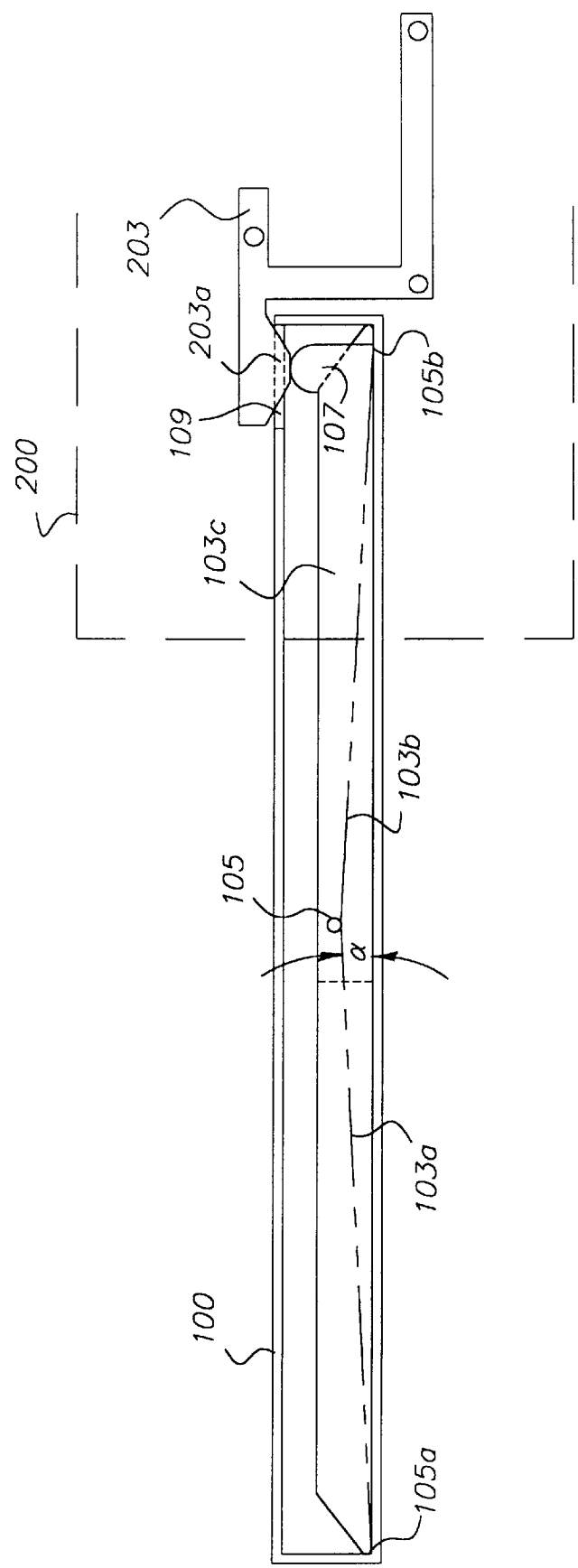
FIGS. 9 and 10 illustrate further features of the linkage assembly of FIG.7.
Figure 10:
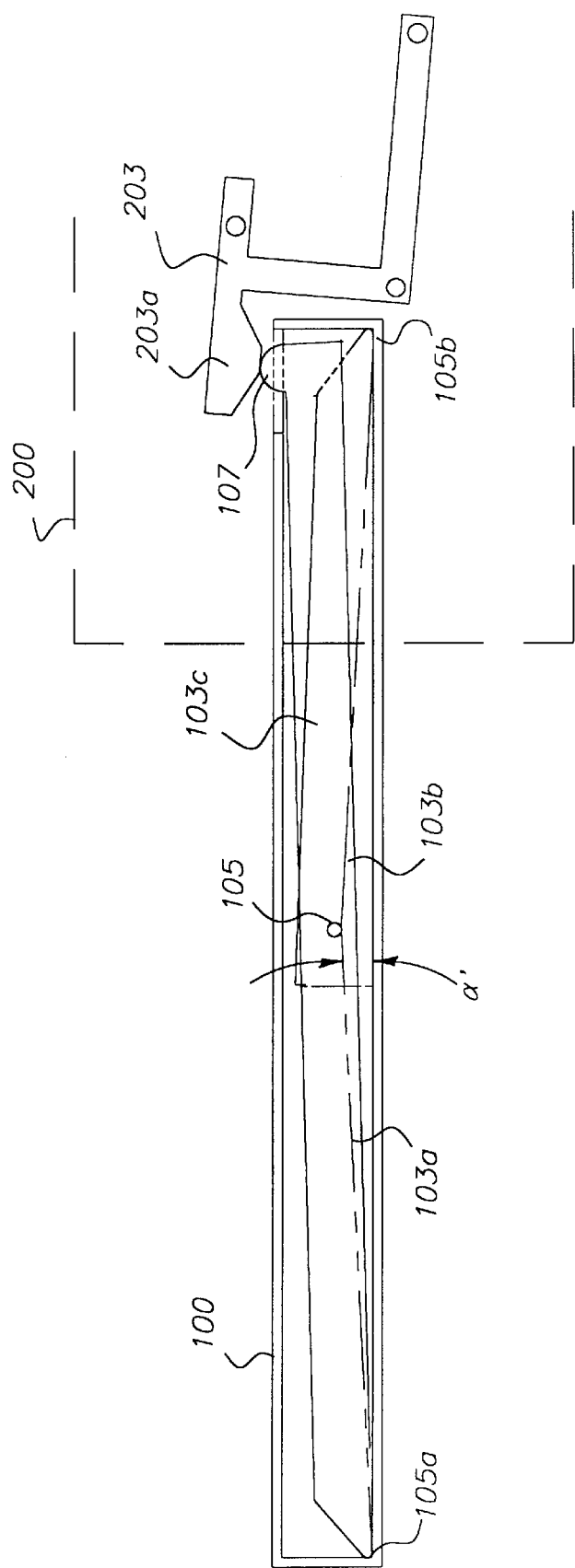

FIGS. 7, 8(a), 8(b), 9 and 10 illustrate a further embodiment of the present invention. More specifically, FIGS. 7, 8(a) and 8(b) illustrate an apparatus for adjusting a crushing roller force which instead of utilizing an electromagnetic or extension spring driven by a stepper motor as described, utilizes a linkage assembly within a media cartridge. FIG. 7 illustrates a cartridge 100 which holds a stack of media 101. Cartridge 100 in FIG. 7 includes a linkage assembly or mechanism 103 which includes sections that are pivoted at a pivot point 105. Cartridge 100 includes an access slot 109 which permits a knob 107 attached to a link section 103c of linkage assembly 103 to extend therethrough. When inserted into an image forming device or printer 200 (similar to image forming device 15 as described), area 111 of cartridge 100 will be inserted into the printer so as to define an inserted position in which media from cartridge 101 is conveyed into printer 200. Furthermore, it is noted that cartridge 100 includes a light lock door end to prevent light from entering into cartridge 100. With reference to FIGS. 9–10, in order to be responsive to humidity conditions inside of cartridge 100, linkage assembly 103 further includes link sections 103a, 103b which are linked at pivot point 105 and can be made of a material, for example, nylon, that expands at high humidity. Link section 103c including knob 107 is attached to link sections 103a, 103b via pivot point 105 and although not required, linkage section 103c can also be made out of a material that expands.

Therefore, under low humidity conditions as illustrated in FIG. 9, linkage assembly 103 will remain at a rest position and thus knob 107 will not extend through slot 109. When humidity in media cartridge 100 increases above a predetermined value linkage sections 103a, 103b will expand, and therefore, pivot about pivot point 105 which is a moving pivot point, as well as pivot points 105a 105b which are fixed. This will increase a toggle angle $\alpha$ as illustrated in FIG. 9 from a first value, to a second value $\alpha'$ as illustrated in FIG. 10 which is larger than $\alpha$. This causes link section 103c to move upward causing knob 107 to extend through slot 109 as illustrated in FIG. 10. In general, link sections 103a, 103b should be made of a material that expands in length by approximately a value of 0.5%.

With the use of the embodiment of FIGS. 7–10, printer 200 will include a lever assembly 201 (FIGS. 8(a)–8(b)) which cooperates with linkage assembly 103 to adjust the crushing force on the microcapsules of the photosensitive media. More specifically, with reference to FIGS. 8(a)–8(b), lever assembly 201 in printer 200 includes a printer link 203 movably attached to a lever arm 205 by way of a spring 207.

Printer link 203 includes a knob 203a which cooperates with knob 107 of linkage assembly 103. Printer link 203 rests against a stop 209 (before cartridge 100 is inserted into printer 200) and further includes a spring 211 to control movement of link 203.

Lever arm 205 is analogous to lever arm and beam arrangement described in, for example, FIGS. 3(a)–(3c). More specifically, lever arm 205 includes a beam 215 which abuts against a surface of photosensitive media 219 and forms a flat nip with a crushing roller 217 in the same manner as described, with respect to, for example, FIGS. 3(a)–3(c). Lever arm 205 and beam 215 are upwardly urged by way of a main spring 220. As also illustrated in FIGS. 8(a)–8(b), printer link 203 is pivoted at point 221, while lever arm 205 is pivoted at point 222.

Therefore, under low humidity conditions as illustrated in FIG. 9, linkage assembly 103 will remain at a rest position, such that knob 107 does not extend through slot 109. In this position, knob 203a will rest on knob 107, and will not apply an additional upward force onto lever arm 205. Thus, lever arm 205 and beam 215 will apply an initial force or a reduced force onto photosensitive media 219 by way of main spring 220. When the humidity increases as illustrated in FIG. 10, linkage sections 103a, 103b will expand to thus increase toggle angle α to α' and move pivot point 105 upward. Movement of pivot point 105 upward will move link section 103c upward to extend knob 107 through slot 109 so as to urge knob 203a upwardly. The urging of knob 203a upwardly will move printer link 203 in a clockwise direction about pivot point 221 to urge spring 207 upward. The urging of spring 207 upward will urge lever arm 205 and beam 215 in a clockwise direction about pivot point 222, so as to provide a further force against photosensitive media 219 by beam 215, and therefore increase the amount of crushing force applied to photosensitive media 219.

Thus, the embodiment of FIGS. 7–10 provides for a mechanical method of adjusting the printing force based on humidity within the media cartridge. The linkage fits inside of the cartridge within the side of the media cartridge and provides a means for adjusting a lever within the printer, which in turn adjusts a printing roller force. Further, the combination of the cartridge and the image forming device would provide for an image forming assembly or arrangement.

Figure 11A:
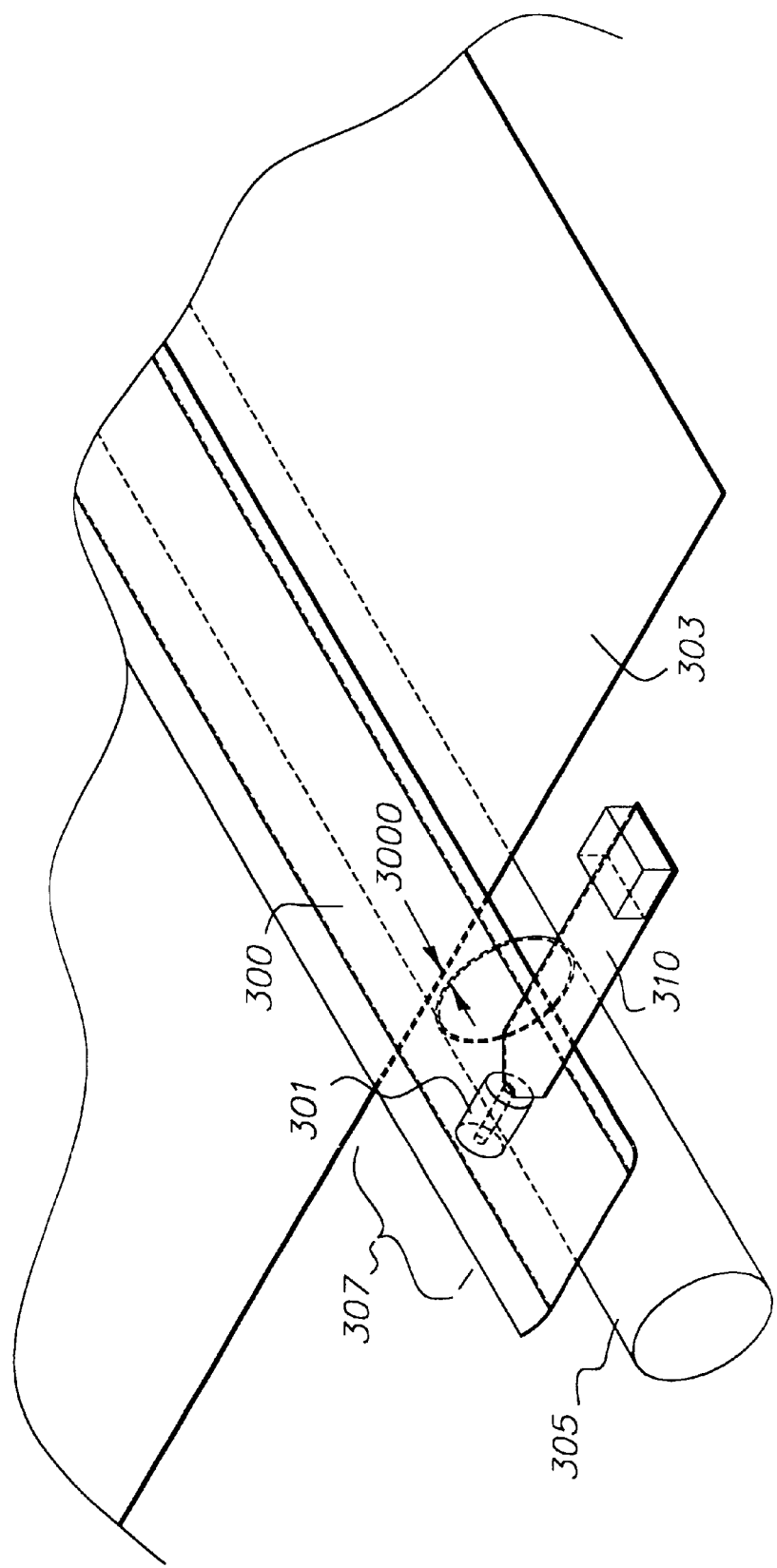
FIGS. 11(a)–11(b) illustrate further features of the image forming device of the present invention including the use of a pressure strip.
Figure 11B:
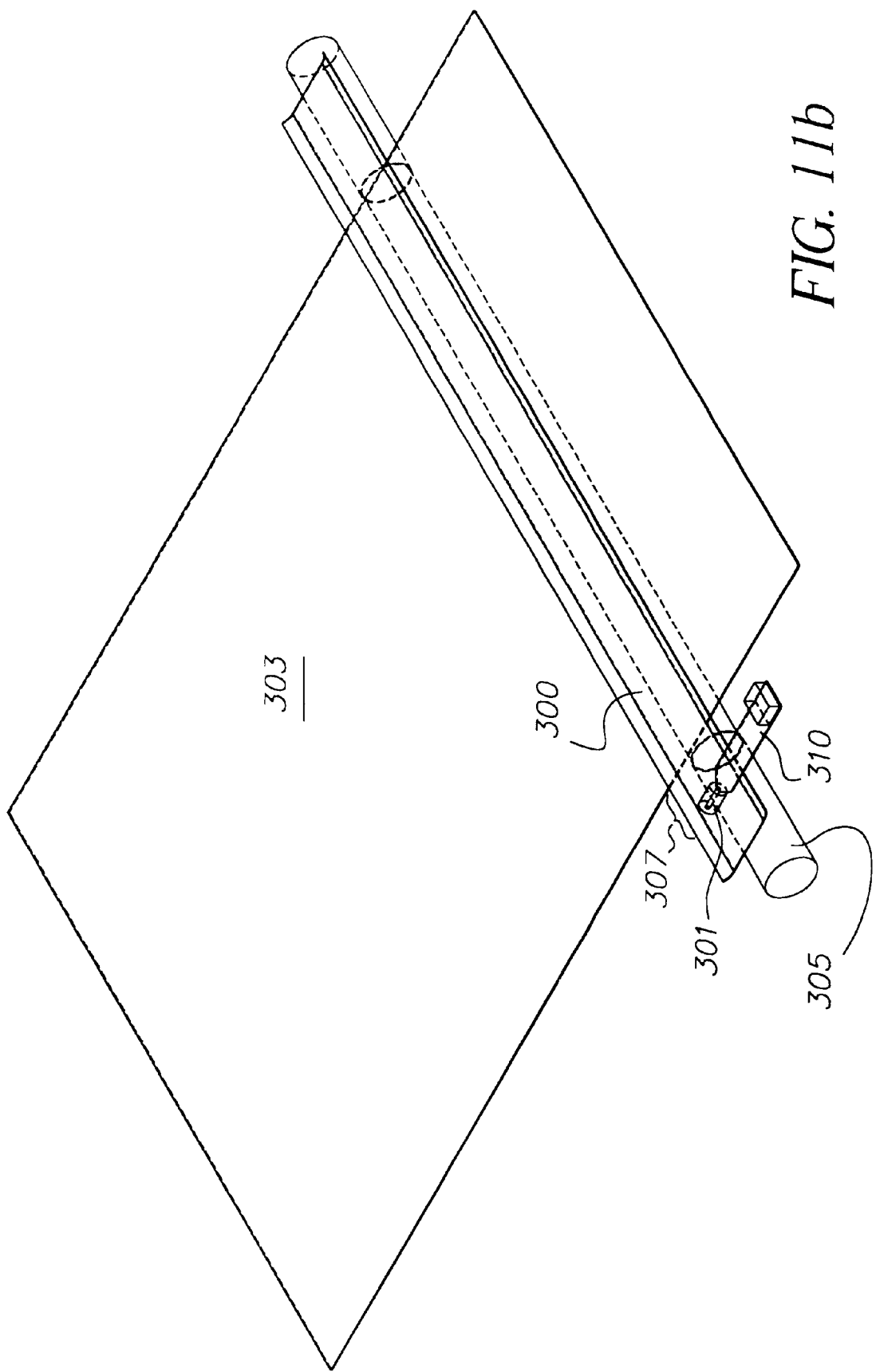
Figure 12:
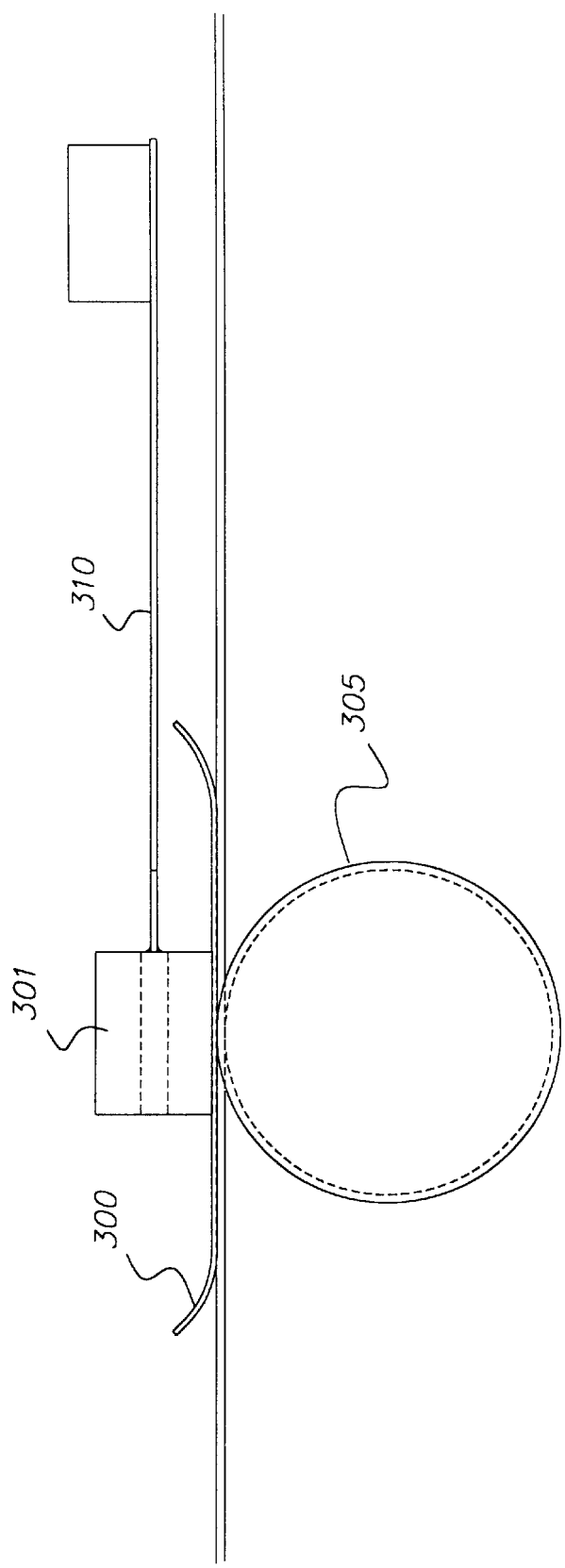
FIG. 12 is a side view of the pressure strip of FIGS. 11(a), 11(b).

FIGS. 11(a), 11(b) and 12 illustrate a further embodiment of the present invention. With respect to utilizing a crushing force on photosensitive media having microcapsules by way of crushing rollers and a beam, there is a possibility of marking the media. In the embodiment of FIGS. 11(a), 11(b) and 12, a pressure strip 300 made out of, for example, a polyester such as polyethylene terephtalate material can be used. As an example, pressure strip 300 can be approximately 0.006 inches thick. Pressure strip 300 would be provided between crushing roller 301 and photosensitive media 303 with beam 305 being provided on the opposite side of media 303. Pressure strip 300 would also extend beyond the widthwise edges of media 303. During printing, crushing roller 301 travels along a widthwise direction of photosensitive media 303 and travels outside the edges of photosensitive media 303. Without flexible strip 300, the edges of the media would provide for a step for the crushing roller as the crushing roller extends from a section 307 above the beam which does not include the photosensitive media 303 to a section above the beam which includes photosensitive media 303 therebetween or vice versa. The provision of pressure strip 300 between crushing roller 301 and photosensitive media 303 provides for a smooth passage for crushing roller 301 over photosensitive media 303, and in addition, provides for a smooth transition between the section 307 which does not include photosensitive media 303, i.e., outside the edges of photosensitive media 303, and the section which includes media 303. Therefore, when crushing roller is placed at, for example, a parking area or shoulder outside the edges of photosensitive media 303 (section 307), flexible strip 300 provides for a bridge between section 307 and photosensitive media 303. Further, the addition of pressure strip 300 permits a full width imaging to be performed as opposed to performing imaging only within a border of the media. More specifically, crushing roller 301 including pressure strip 300 positioned thereunder, is designed to crush media to the edge of the media and move beyond the edge for indexing the media. Flexible pressure strip 300 provides a bridge for crushing roller 301 to roll over with a minimal gap 3000 (FIG. 11(a)) and low force.

In a further feature of the invention as illustrated in FIG. 12, crushing roller 301 can be mounted onto a leaf spring 310 to apply crushing pressure onto photosensitive media 303. Leaf spring 310 can be attached to crushing roller 301 to slide with the crushing roller 301 along the widthwise direction of the photosensitive media 303, while applying a crushing force onto media 303.

In a further feature of the invention, flexible pressure strip 300 could be fixed at each widthwise end to prevent unwanted movement of the strip. Also, strip 300 could be made of a low friction wear material.

In a still further feature of the invention, the light exposure by imaging head 25 or the temperature of heater 29 can be adjusted (see, for example, EP 08644301 A1). In the present invention, the adjustment of the light exposure or the temperature would be based on the humidity sensed by sensor 33 (FIG. 1); sensor 87 (FIG. 6(a)); sensor 87' (FIG. 6(b)) or device 600 (FIG. 6(c)). In this scenario, the value of the current or voltage which is supplied to the LED's of the imaging head or the heating element of the heater would be adjusted based on the sensed humidity value.

In a still further feature, as previously described, printing speed can be adjusted based on the sensed humidity condition. In this scenario, controller 30 can provide a signal to motor 37 to control the printing speed based on the measured humidity.

The invention has been described in detail with particular reference to certain preferred embodiments thereof, but it will be understood that variations and modifications can be effected within the spirit and scope of the invention.

What is claimed is:

1. A photosensitive media cartridge comprising:
   a housing for holding a stack of photosensitive media; and
   an ambient condition sensor mounted within said housing for sensing ambient conditions in said housing and providing an ambient condition signal indicative thereof, wherein a development of the photosensitive media is based on the sensed ambient condition.

2. A cartridge according to claim 1, wherein said housing comprises a first section and a second section which are attachable to each other.

3. A cartridge according to claim 2, wherein said ambient condition sensor comprises:
   a spring plate attached to one of said first and second sections of said housing;
   a first contact plate having a first electrode, said first contact plate being mounted on said spring plate;
   a sampling material mounted on said first contact plate; and a second contact plate having a second electrode, said second contact plate being mounted on said sampling material.

4. A cartridge according to claim 3, wherein said sampling material is responsive to humidity conditions within said housing, such that a change in humidity value within said housing causes a change in a measured capacitance of said sampling material.

5. A cartridge according to claim 1, wherein said photosensitive media comprises microcapsules which encapsulate imaging material.

6. A cartridge according to claim 5, wherein said imaging material comprises coloring material, and said cartridge is adapted to be inserted into a printer having a pressure assembly for applying pressure to said photosensitive medium to crush said microcapsules and develop a latent image on said photosensitive medium.

7. A cartridge according to claim 6, wherein when said cartridge is inserted in the printer, said ambient condition sensor is adapted to provide said ambient condition signal to the pressure assembly to control an amount of pressure applied to the photosensitive medium in said printer based on the sensed ambient condition in said cartridge.

8. A cartridge according to claim 7, wherein said ambient condition is a sensed humidity in said cartridge.

9. A cartridge according to claim 3, wherein said first and second electrodes extend from an interior of said cartridge to an exterior of said cartridge.

10. A cartridge according to claim 1, wherein said cartridge is adapted to be inserted into a printer having an imaging head and a heater.

11. A cartridge according to claim 10, wherein a light exposure of said imaging head is adjusted based on said ambient condition.

12. A cartridge according to claim 10, wherein a temperature of said heater is controlled based on said ambient condition.

13. A cartridge according to claim 10, wherein a printing speed of said printer is controlled based on said ambient condition.

14. A cartridge according to claim 1, wherein said ambient condition sensor comprises a substrate with conductive terminals and a humidity sensitive material coated on the substrate.

\* \* \* \* \*